United States Patent [19]

Schaub et al.

[11] 4,180,677

[45] Dec. 25, 1979

[54] NOVEL PROSTAGLANDINS

[75] Inventors: Robert E. Schaub, Upper Saddle River, N.Y.; Martin J. Weiss, Oradell, N.J.

[73] Assignee: American Cyanamid Company, Stamford, Conn.

[21] Appl. No.: 846,487

[22] Filed: Oct. 28, 1977

Related U.S. Application Data

[60] Continuation-in-part of Ser. No. 719,650, Sep. 1, 1976, abandoned, which is a division of Ser. No. 555,219, Mar. 4, 1975, Pat. No. 3,993,674, which is a division of Ser. No. 353,152, Apr. 20, 1973, Pat. No. 3,884,969.

[51] Int. Cl.² ............................................ C07C 177/00
[52] U.S. Cl. ............................. 562/500; 260/410.9 R; 260/413; 560/118
[58] Field of Search ........................ 560/118; 562/500; 260/413, 410.9 R

[56] References Cited

U.S. PATENT DOCUMENTS

| 3,880,883 | 4/1975 | Caton et al. ...................... 260/340.9 |
| 3,884,969 | 5/1975 | Schaub et al. .................... 260/514 D |
| 4,024,181 | 5/1977 | Babej et al. ..................... 260/514 D |

*Primary Examiner*—Robert Gerstl

[57] ABSTRACT

This disclosure describes novel 15-hydroxy prostanoic acid derivatives having anti-ulcer, bronchodilator, and hypotensive activity.

47 Claims, No Drawings

NOVEL PROSTAGLANDINS

CROSS REFERENCE TO RELATED APPLICATION

This application is a continuation-in-part of our co-pending application Ser. No. 719,650, filed Sept. 1, 1976, which is in turn a Divisional of our application Ser. No. 555,219, filed Mar. 4, 1975, now U.S. Pat. No. 3,993,674, which is in turn a Divisional of our application Ser. No. 353,152, filed Apr. 20, 1973 now U.S. Pat. No. 3,884,969.

BRIEF SUMMARY OF THE INVENTION

This invention relates to novel 15-hydroxy prostanoic acids and derivatives, as well as to intermediates and methods for their preparation. The novel prostanoic acids and derivatives of this invention may be represented by the following general formula:

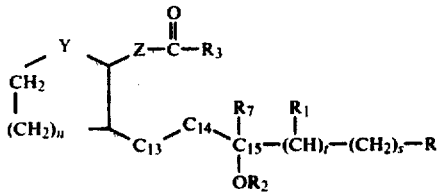

wherein Y is a divalent radical selected from the group consisting of those of the formulae:

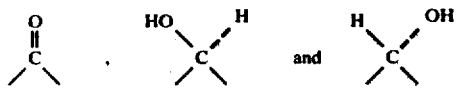

and Z is a divalent radical selected from the group consisting of those of the formulae:

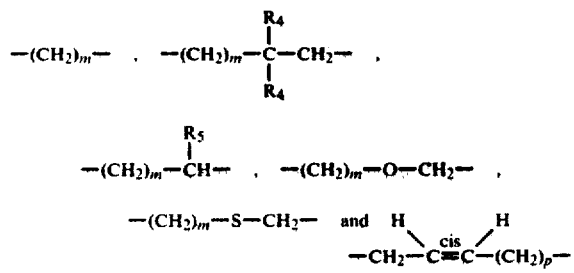

wherein m is an integer from 3 to 8, inclusive, p is an integer from 2 to 6 inclusive, $R_4$ is an alkyl group having up to 3 carbon atoms, and $R_5$ is an alkyl group having up to 3 carbon atoms, a fluorine atom or a phenyl group; the moiety —$C_{13}$—$C_{14}$— is ethylene, or trans-vinylene; $R_1$ is selected from the group consisting of lower alkyl groups having up to 3 carbon atoms; $R_2$ is selected from the group consisting of hydrogen, triphenylmethyl, and mono- or di-methoxy substituted triphenylmethyl; $R_3$ is hydroxyl or alkoxy having from one to twelve carbon atoms; $R_7$ is selected from the group consisting of hydrogen and lower alkyl groups having up to 3 carbon atoms with the proviso that when $R_7$ is alkyl then $R_2$ is hydrogen; n is an integer having the value one or two; s is zero or an integer having the value one to five inclusive, t is zero or one; and R is selected from the group consisting of cycloalkyl groups having from three to nine carbon atoms; cycloalkenyl groups having from five to nine carbon atoms; mono or dilower alkyl substituted cycloalkyl groups having from three to eight carbon atoms in the ring, mono or dilower alkyl substituted cycloalkenyl groups having from five to eight carbon atoms in the ring and adamantyl groups; with the proviso that only one double bond or cyclopropyl group can be immediately adjacent to $C_{15}$; and with the additional proviso that when n is one, Z is —$(CH_2)_m$— and R is a saturated cycloalkyl or adamantyl group then the sum of s and t is at least one.

DETAILED DESCRIPTION OF THE INVENTION

Also embraced within the scope of the present invention are the non-toxic, pharmaceutically acceptable salts of the novel compounds of the present invention when $R_3$ is hydroxy. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine, tri($\beta$-hydroxyethyl)amine, procaine and the like).

The compounds of this invention include all possible optical isomers. The novel compounds of the present invention are usually obtainable as oils having characteristic absorption spectra. They are relatively insoluble in water but are relatively soluble in common organic solvents such as ethanol, ethyl acetate, dimethylformamide, and the like. The cationic salts of the compounds when $R_3$ is hydroxy are, in general, white to yellow crystalline solids having characteristic melting points and absorption spectra. They are relatively soluble in water, methanol, and ethanol but are relatively insoluble in benzene, diethyl ether and petroleum ether.

The novel compounds of the present invention may be readily prepared from certain cycloalkenone intermediates some of which may be represented by the following general formula:

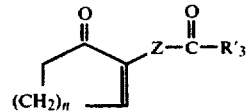

wherein Z and n are as defined above, and $R'_3$ has all the possibilities given above for $R_3$ except that it is not hydroxyl. The preparation of certain of these cycloalkenones is described in Belgium Pat. No. 786,215 (granted and opened to inspection Jan. 15, 1973). Others of the requisite cycloalkenones are prepared by extension of the methods described therein.

The preparation of the cycloalkenone intermediates (X, XI) bearing a cis double bond in the carboxylic acid side chain can be accomplished by the sequences illustrated in Flowsheets A or B. In Flowsheet A which follows, n and p are as hereinabove defined.

FLOWSHEET A

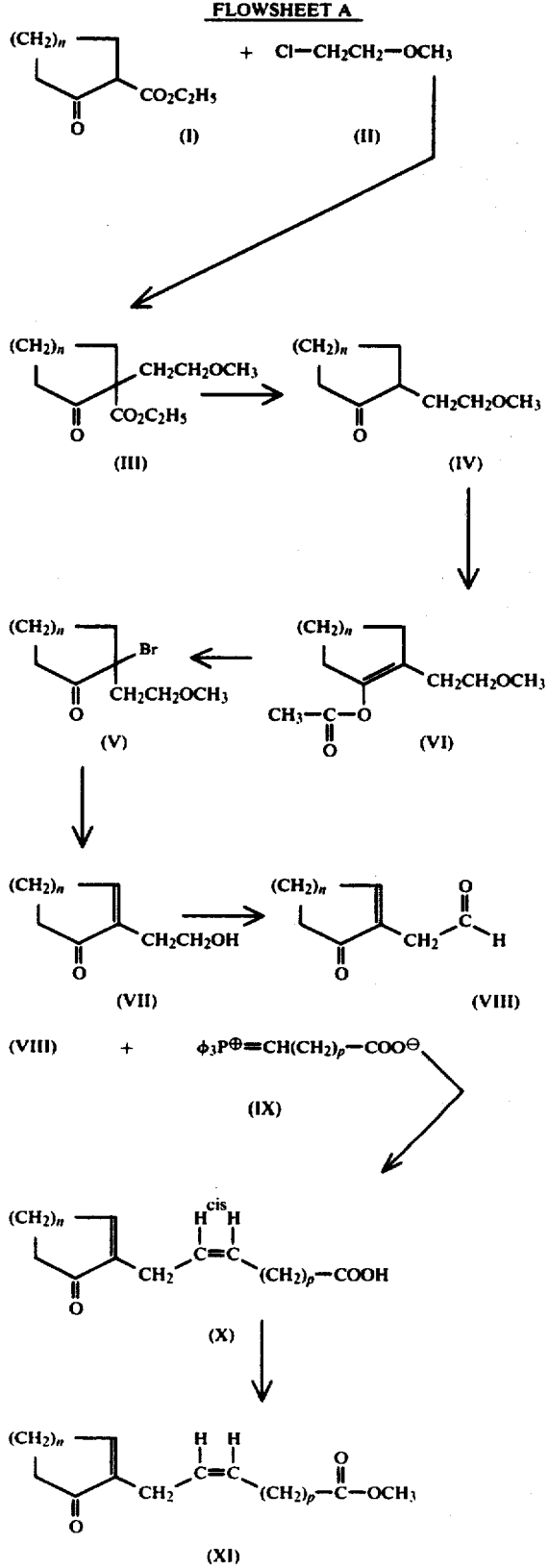

In the above Flowsheet A, the sequence wherein a 2-carbalkoxycycloalkanone (I) is transformed to a 2-(β-hydroxyethyl)cycloalk-2-en-1-one (VII) is carried out in the manner described in Belgium Pat. No. 786,215 citered hereinabove. Methyl ether cleavage of the corresponding 2-(β-methoxyethyl)cycloalkenone is achieved by treating with boron tribromide. Oxidation of the alcohol with Collins reagent (chromium trioxide-pyridine complex) in methylene chloride under anhydrous conditions provides the aldehyde (VIII), which is then treated in anhydrous dimethylsulfoxide with the ylid (IX) prepared from an (ω-carboxyalkyl)triphenyl phosphonium bromide and sodium hydride. The use of dimethylsulfoxide as a solvent for this reaction leads to the predominant formation of the desired cis double bond in (X). The acid function in (X) can be esterified in the usual fashion; with diazomethane, the methyl ester (XI) is obtained.

Cyclopentenones such as (XVI) may also be prepared by the sequence illustrated in Flowsheet B, which follows and in which p is as hereinabove defined.

FLOWSHEET B

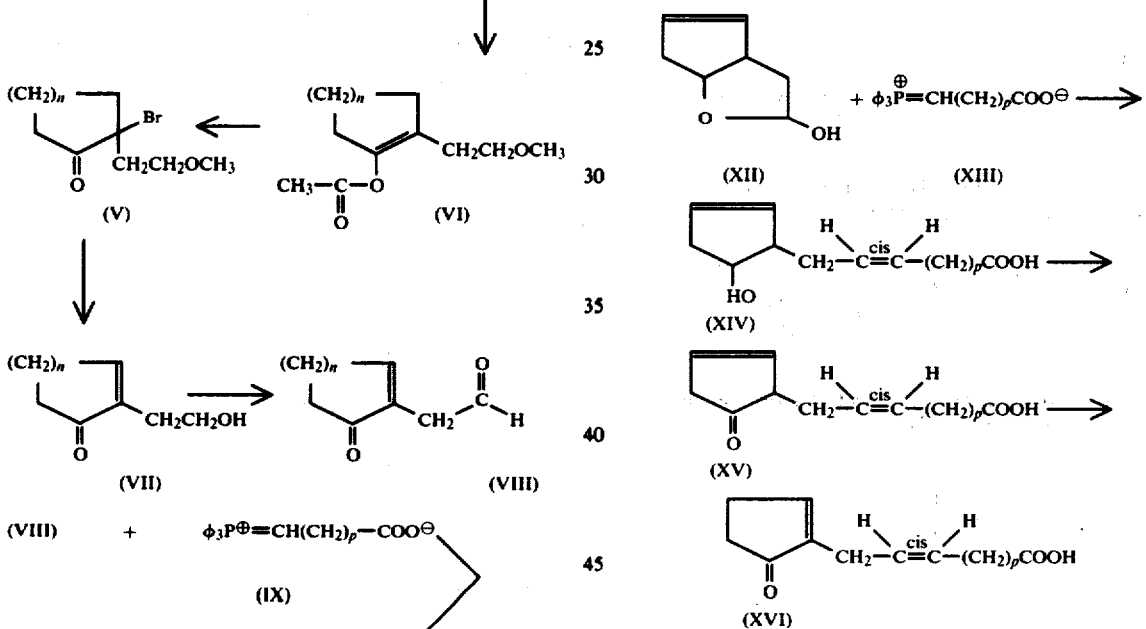

In Flowsheet B, above the bicyclic hemiacetal (XII) [P. A. Grieco, Journ. Org. Chem., 37, 2363 (1972)] is treated with ylid (XIII) to give the 1-hydroxy-3-cyclopentene (XIV). Oxidation with Jones reagent gives the corresponding ketone (XV), which on base treatment furnishes the required cyclopentenone (XVI), which can then by esterified in the usual manner.

The 9-keto-13-trans-prostenoic acids and esters of this invention may be prepared by the novel conjugate addition process outlined in the Flowsheet C which follows. In Flowsheets C, R, $R_1$, Z, $R_3$, $R'_3$, n, s and t are as defined hereinabove; $R_8$ is a lower alkyl group (each of the three $R_8$ radicals bonded to an aluminum atom does not necessarily have to be the same), $R'_2$ has all the possibilities given hereinabove for $R_2$ except hydrogen, and R' has all the possibilities given hereinabove for R except that it does not include cycloalkenyl, cyclopropyl or adamantyl groups.

FLOWSHEET C

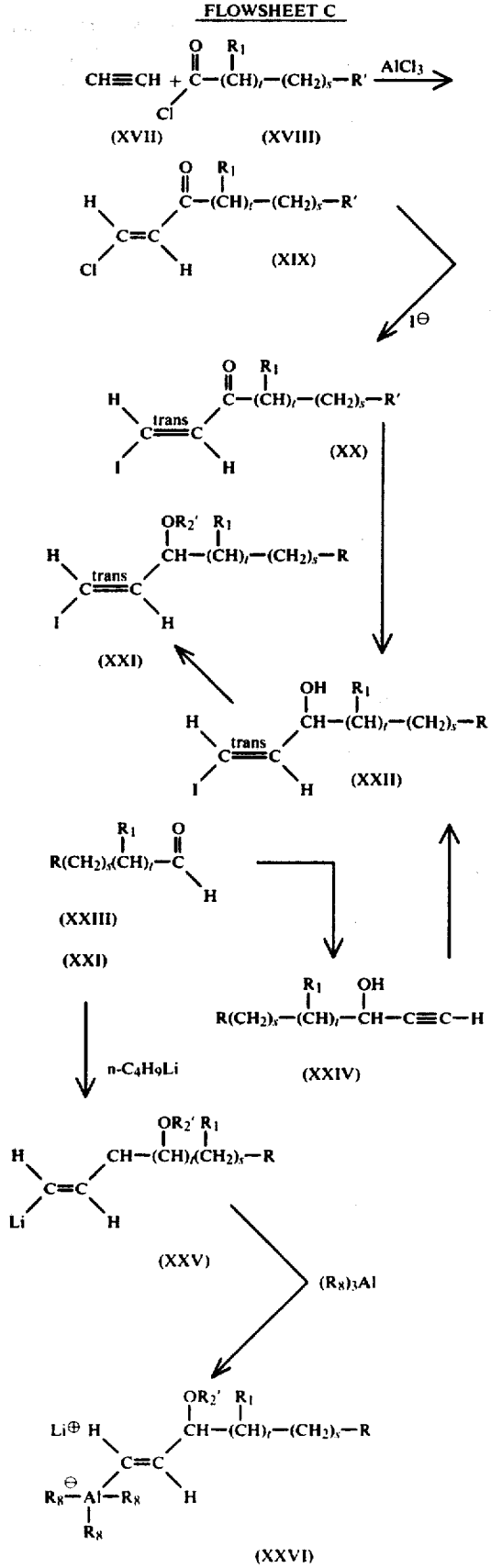

-continued
FLOWSHEET C

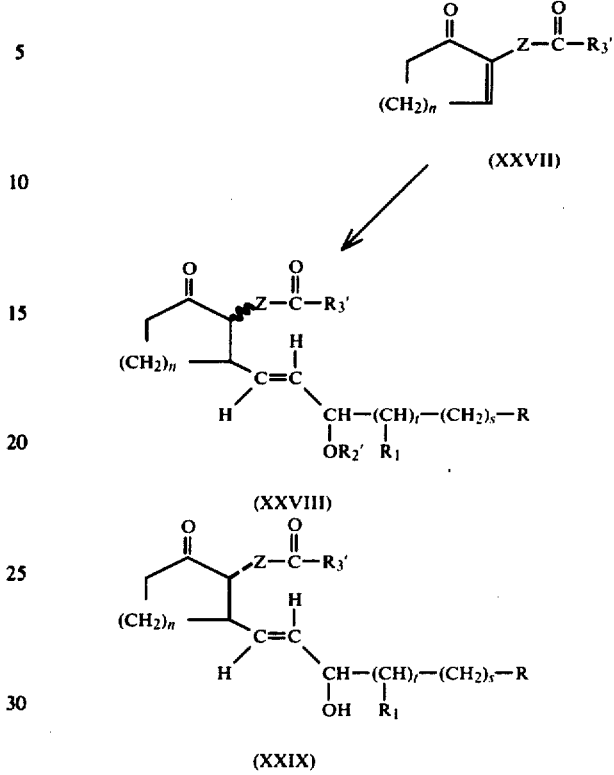

In accordance with the reaction scheme of Flowsheet C, acetylene (XVII) is treated with a cycloalkyl, or a cycloalkyl substituted alkyl acid chloride (XVIII) in the presence of aluminum trichloride to provide the 1-chloro-3-keto-trans-1-alkene (XIX). Interchange with sodium iodide, preferably in a ketone solvent such as acetone, provides the corresponding trans-vinyl iodide (XX). Reduction of the keto function in (XX) with sodium borohydride furnishes the alcohol (XXII), which is then blocked with the triphenylmethyl group or a triphenylmethyl group substiuted with one or two methoxy groups. Introduction of the methoxy group(s) increases the rate of etherification and more importantly increases the facility by which acid hydrolysis later cleaves the trityloxy group. Blocking the hydroxy function can also be accomplished with a trialkylsilyl group, a tetrahydropyranyl group, α-alkoxyethyl group or any other hydroxy blocking group compatible with the conjugate addition process described below and which can later be removed by conditions to which the final products (XXIX) are stable.

Alternatively, trans-1-alkenyl iodide (XXII) can be obtained from the aldehyde (XXIII) by reaction of (XXIII) with lithio acetylide and treatment of the resulting 3-hydroxy terminal acetylene (XXIV) with disiamylborane followed with trimethylamine oxide and then with iodine and sodium hydroxide solution.

Submission of the blocked vinyl iodide (XXI) to metal interchange with an alkyl lithium e.g. n-butyl lithium, at very low temperatures, e.g. −78° C., provides the vinyl lithium derivative (XXV), the trans-configuration of the double bond being retained. After one to four hours, addition of a trialkyl aluminum, preferably trimethyl aluminum, to the solution of the lithio derivative (XXV) furnishes the key alanate intermediate (XXVI), also with retention of the trans-configuration of the double bond. The cycloalkenone (XXVII) dissolved in ether or other non-prototropic solvent, is then added to the alanate solution. The resulting solution is allowed to warm to room temperature and is kept for about six to eighteen hours at ambient temperatures. The carboxylic acid group in cycloakenone (XXVII) is blocked as an ester. Interaction of alanate (XXVI) with cycloalkenone (XXVII) results in the transfer of the trans-1-alkenyl ligand in (XXVI) with retention of the trans-configuration to the cycloalkenone (XXVII) furnishing, after quenching the reaction solution, the 1,4-conjugate addition product (XXVIII). In (XXVIII) we are not certain of the relative configuration of the side-chains to each other. The situation is indicated in structure (XXVIII) by the 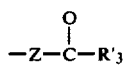 bond between the ring and the $$-Z-\overset{O}{\underset{\|}{C}}-R'_3$$

chain and is indicated in the nomenclature of the compounds involved by the designation 8ξ. In any event deblocking to (XXIX) with acid, e.g. treatment with acetic acid:tetrahydrofuran:water in the ratio of 3:1:1 at 35°–45° C. for some three to forty-eight hours, results in the trans-relationship between the chains. This procedure results in de-O-tritylation as well as hydrolysis of tetrahydropyranyl and trialkylsilyl groups. Alkyl esters are not cleaved by this procedure. Saponification can be accomplished by the usual alkaline procedures.

In order to ensure a trans-relationship in (XXVIII) these products can be submitted to conditions known in the literature to equilibrate cis-8-iso PGE₁ to a mixture containing about 90% of the trans product. These conditions involve treatment with potassium acetate in aqueous methanol for 96 hours at room temperature.

The 13-dihydro derivatives ($C_{13}$-$C_{14}$ is ethylene) of this invention can be prepared by reduction of the $\Delta^{13}$ function in the corresponding 13-prostenoic acids or esters. This reduction can be accomplished by catalytic reduction, preferably at low pressure with a noble metal catalyst in an inert solvent at ambient temperatures.

The 13-dihydro derivatives can also be prepared by treating cycloalkenones of formula (XXVII) with Grignard reagent (XXX) in the usual manner in the presence of a catalyst such as the tributylphosphine cuprous iodide complex. The 15-O-t-butyl blocking group in the conjugate addition product can be efficiently removed by treatment with neat trifluoroacetic acid in the cold for about twenty minutes followed by brief treatment with aqueous ammonia because of potential 15-O-trifluoracetylation.

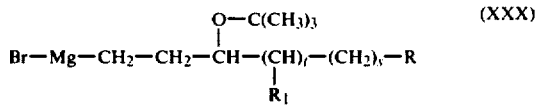

(XXX)

The 9-keto derivatives of this invention can be converted to the corresponding 9-hydroxy derivatives. If this conversion is effected with sodium borohydride, the product is a mixture of 9α- and 9β-hydroxy derivatives (XXXII) and (XXXIII), respectively as set forth in the following reaction scheme of Flowsheet D which follows and in which Z, $R_3$, n, s, t, R, $R_6$, $R_7$ and $C_{13}$-$C_{14}$ are as hereinabove defined.

When the reduction of the 9-keto function is carried out with lithium perhydro-9-boraphenyalkyl hydride [H. C. Brown and W. C. Dickason, *Journ. Amer. Chem. Sec.*, 92 709 (1970)] the product is at least predominantly the 9α-hydroxy derivative (XXXII), wherein the 9-hydroxy group is cis to the side-chain attached to $C_8$ and to the 11-substituent if present. In accordance with accepted convention, an α-substituent at the 8-, 9-, 11- or 12-positions is behind the plane of the paper whereas a β-substitutent at these positions is in front of the plane of the paper. This is usually represented by a - - - bond for an α-substituent, a ―― bond for a β-substituent, and a 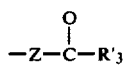 bond where both are indicated.

FLOWSHEET D

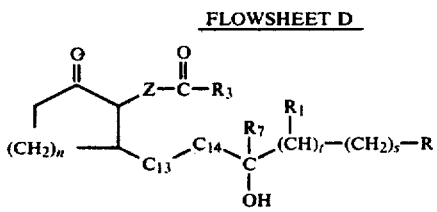

(XXXI)

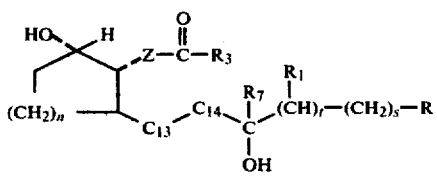

(XXXII)

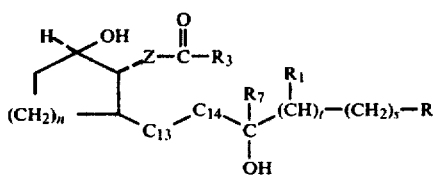

(XXXIII)

A useful procedure for the introduction of the 15-lower alkyl group ($R_7$) is illustrated by the sequences of Flowsheet E, which follows.

FLOWSHEET E

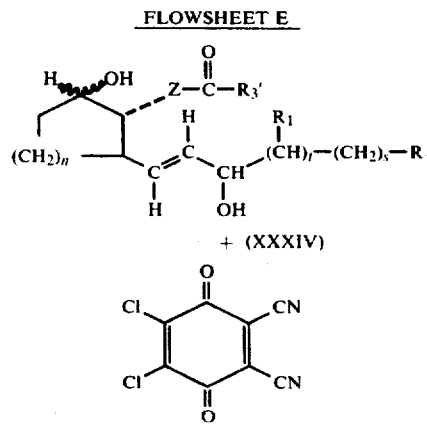

-continued
FLOWSHEET E

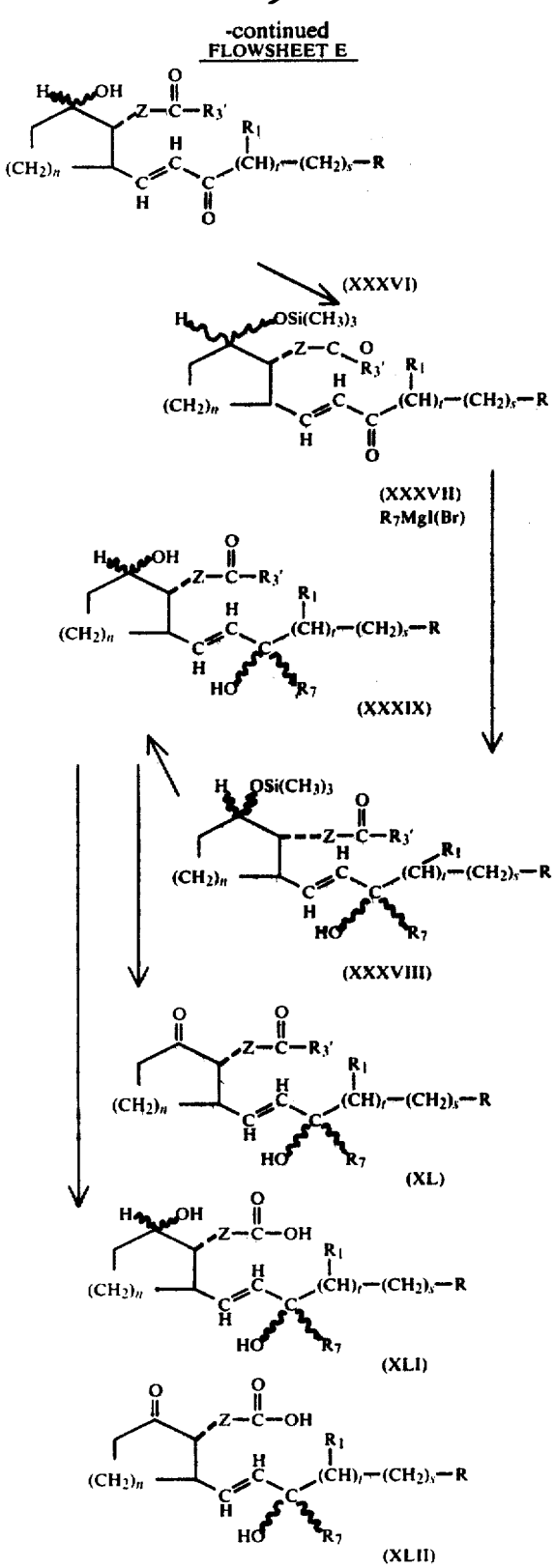

In Flowsheet E above R, $R_1$, $R'_3$, $R_7$ n, s, t and Z are as hereinabove defined. In the sequence depicted in Flowsheet E the 9,15-diol (XXXIV) is treated with 2,3-dichloro-5,6-dicyanobenzoquinone (DDQ) (XXXV), which preferentially oxidizes the allylic alcohol function at $C_{15}$ to give the 15-keton (XXXVI). Blocking of the remaining hydroxy function as a trimethylsilyl ether gives (XXXVII) which is reacted with the alkyl Grignard, $R_7MgI$, to give the 15-alkyl-15-hydroxy derivative (XXXVIII). Hydrolysis of the silyl ether blocking group then furnishes the diol ester (XXXIX), saponification of which gives (XLI). Oxidation of the secondary 9-hydroxy function in (XXXIX) provides the 15-alkyl-9-oxo ester (XL), saponification of which furnishes (XLII).

This procedure leads to two epimeric $C_{15}$ alcohols and these are separable by chromatograhic procedures.

This invention also embraces the novel and useful intermediates illustrated by the generic formula A below, in which $R'_2$, s, t, $R_1$ and R are as hereinabove defined with the only proviso being that when R is a 3-numbered carbocycle the sume of s and t is at least one; and K is iodine, lithium, or lithio tri (lower alkyl) aluminate

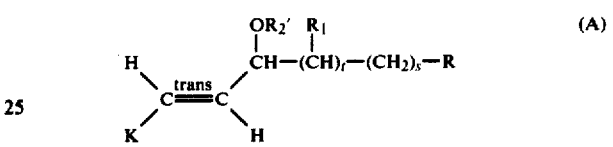

The novel compounds of the present invention have potential utility as hypotensive agents, anti-ulcer agents, agents for the treatment of gastric hypersecretion and gastric erosion, periodontal disease, glacoma, uveitis, bronchodilators, antimicrobial agents, anticonvulsants, abortifacients, agents for the induction of labor, agents for the induction of menses, fertility-controlling agents, central nervous system regulatory agents, salt and water-retention regulatory agents, diuretics, fat metabolic regulatory agents, serum-cholesterol lowering agents, anti-inflammatory agents and as agents for the inhibition of platelet aggregation. Certain of the novel compounds of this invention possess utility as intermediates for the preparation of other of the novel compounds of this invention.

The compounds of this invention provide protection against the ulcerogenic properties of indomethacin. This assay was carried out in the following manner.

Rats were starved for 48 hours (water was given ad libitum). Indomethacin (20 mg./kg. of body weight) was administered by the subcutaneous route and one-half the dose of the test compound was administered by gavage at the same time. After three hours, the second half of the test compound was administered also be gavage. Five hours after the administration of indomethacin the animals were decapitated and the stomachs removed. The stomachs were washed with distilled water, blotted on gauze, cut along the larger curvature, and the contents rinsed with distilled water. The stomachs were spread out, pinned on a cork and visualized under magnifying glass for ulcers. The criteria for scoring of ulcers was as previously reported. [Abdel-Galil et al. *Brit. J. Pharmac. Chemotherapy* 33:1–14 (1968)].

Score
0-Normal stomach
1-Petechial hemorrhage or pin point ulder
2-1 or 2 small ulcers
3 Many ulcers, a few large
4-Many ulcers, mainly large Control animals treated with indomethacin but not test compound consistenly give scores of about 3.0. Control animals treated with neither indomethacin nor test compound gives scores of about 0.5–0.8. The results obtained in this assay with typical compounds of the present invention are set forth in Table A below. Compounds producing a lowering of the control score by 0.5 or more are considered to be active.

TABLE A

| Compound | Total Oral dose; mg./kg. of body weight | Score Treated | Control |
|---|---|---|---|
| 9-oxo-15-hydroxy-17,20-methane-13-trans-prostenoic acid | 12.5 | 1.8 | 2.8 |
| 9-oxo-15-epi-hydroxy-17,20-methano-13-trans-prostenoic acid | 25.0 | 1.7 | 3.0 |

Bronchodilator activity was determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, *Arzneimittel-Forschung*, 18, 995 (1968).]

In the Table which follows bronchodilator activity for representative compounds of this invention against one or more of three spasmogenic agents is expressed as an $ED_{50}$ determined from the results obtained with three logarithemic cumulative intravenous doses.

TABLE B

| | Bronchodilator Activity (Konzett Assays) $ED_{50}$, mg./kg. | | |
|---|---|---|---|
| | Spasmogenic Agent | | |
| Compound | 5-hydroxy-tryptamine | histamine | acetyl choline |
| 9-oxo-15-hydroxy-17,20-methano-13-trans-prostenoic acid | $6.3 \times 10^{-3}$ | $1.4 \times 10^{-3}$ | 3.2 |
| 9-oxo-15-epi-hydroxy-17,20-methano-13-trans-prostenoic acid | 3.2 | $206 \times 10^{-3}$ | 3.2 |

This invention will be described in greater detail in conjunction with the following specific examples.

In the following examples, unless otherwise indicated, the products obtained include all possible optical isomers.

EXAMPLES 1

Preparation of 2-(6-carbethoxy-6-fluorohexyl)cyclopent-2-en-1-one

This cyclopentenone is prepared by the procedure described in Belgium Pat. No. 786,215 (Jan. 15, 1973) for the preparation of 2-(6-carbethoxyoctyl)cyclopent-2-en-1-one by substituting diethyl fluoromalonate for diethyl ethylmalonate.

EXAMPLE 2

Preparation of 2-(6-carbethoxy-6-phenylhexyl)cyclopent-2-en-1-one

This cyclopentenone is prepared by the procedure described in Belgium Pat. No. 786,215 (Jan. 15, 1973) for the preparation of 2-(6-carbethoxyoctyl)cyclopent-2-en-1-one by substituting diethyl phenylmalonate for diethyl ethylmalonate.

EXAMPLE 3

Preparation of 2-(6-carbethoxy-heptyl)cyclopent-2-en-1-one

This cyclopentenone is prepared by the procedure described in Belgium Pat. No. 786,215 (Jan. 15, 1973) for the preparation of 2-(6-carbethoxyoctyl)cyclopent-2-en-1-one by substituting diethyl methylmalonate for diethyl ethylmalonate.

EXAMPLE 4

Preparation of 2-(6-carbo-n-butoxyhexyl)cyclopent-2-en-1-one

A solution of 50 g. of 2-(6-carboxyhexyl)cyclopent-2-en-1-one [Bagli et al., Tetrahedron Letters, No. 5, 465 (1966)] in 1400 ml. of n-butanol containing 2.7 g. of p-toluenesulfonic acid monohydrate is allowed to stand at room temperature in a stoppered flask for about 24 hours. The solution is taken to dryness. The residue is taken up in ether and the ethereal solution is washed several times with saline solution, dried with anhydrous magnesium sulfate, and taken to dryness to afford the subject butyl ester.

EXAMPLES 5–7

Treatment of 2-(6-carboxyhexyl)cyclopent-2-en-1-one by the procedure of Example 5 with the appropriate alcohol affords the esters of the following table.

TABLE 1

| Example | Alcohol | Product Ester |
|---|---|---|
| 5 | isopropanol | 2-(6-carboisopropoxyhexyl)-cyclopent-2-en-1-one |
| 6 | methanol | 2-(6-carbomethoxyhexyl)-cyclopent-2-en-1-one |
| 7 | 1-hydroxy-n-decane | 2-(6-carbo-n-decyloxyhexyl)-cyclopent-2-en-1-one. |

EXAMPLE 8

Preparation of 2-carbalkoxy (methyl/ethyl)-2-(2-methoxyethyl-cyclopentan-1-one

Treatment of 2-cyclopentenone carboxylate (mixed methyl and ethyl esters) with 2-methoxyethyl bromide by the method of Example 1 of Belgium Pat. No. 786,215 furnishes the subject compound as an oil, b.p. 90° C. (0.1 mm).

EXAMPLE 9

Preparation of 2-(2-methoxyethyl)cyclopentan-1-one

Heating 8 g. of 2-carboalkoxy (methyl/ethyl)-2-(2-methoxyethyl)cyclopentan-1-one (Example 8) in 8 ml. of 20% aqueous hydrochloric acid at reflux for 3.5 hours and isolating the product by the method of Example 2 of Belgium Pat. No. 786,215 furnishes the subject compound as an oil, b.p. 45°–50° C. (0.02 mm).

EXAMPLE 10

Preparation of 1-acetoxy-2-(2-methoxyethyl)cyclopent-1-ene

The subject compound is prepared from 2-(2-methoxyethyl)cyclopentan-1-one (Example 9) and acetic anhydride by the procedure

EXAMPLE 11

Preparation of 2-(2-hydroxyethyl)-cyclopent-2-en-1-one

The enol acetate of Example 10 is brominated and dehydrobrominated by the method described in Example 28 of Belgium Pat. No. 786,215. The crude product is then dissolved in methylene chloride and is added at −78° C. to a methylene chloride solution containing about seven molar equivalents of boron tribromide. After one hour at −78° C. the solution is allowed to warm to room temperature and is then kept at ambient temperatures for a total of eighteen hours. The mixture is poured into water and extracted with ether. The organic phase is washed with saturated saline solution, then water and is dried. Evaporation of solvents leaves subject product, which is purified by distillation. The combined organic phases are washed with ice cold 5% sodium hydroxide solution, ice cold 5% hydrochloric acid, and saturated sodium chloride solution, dried with anhydrous magnesium sulfate and taken to dryness. Distillation gives a pale yellow oil; λ max 5.85μ (carbonyl group).

EXAMPLE 12

Preparation of 2-formylmethylcycopent-2-en-1-one

Chromium trioxide (0.6 mol) is added to a stirring solution of (1.2 mol) of anhydrous pyridine in 1500 ml. of anhydrous methylene chloride cooled in an ice bath. The deep red suspension is stirred for 15 minutes at 0° C. and 45 minutes at ambient temperature. A solution of 0.15 mol of 2-(2-hydroxyethyl)-cyclopent-2-en-1-one (Example 11) in 50 ml. of methylene chloride is added, all at once, to the suspension. A black terry deposit is formed immediately. After stirring the mixture for 25 minutes at ambient temperature, the methylene chloride is decanted from the tarry precipitate which is then triturated several times with ether.

EXAMPLE 13

Preparation of 2-(6-carboxy-2-cis-hexenyl)-cyclopent-2-en-1-one

A mixture of 0.194 g. (0.007952 mole) of sodium hydride (free of mineral oil) and 5.5 ml. of dimethylsulfoxide is heated to 70° C. until gas evolution ceases under a nitrogen atmosphere. The resulting solution is cooled below room temperature and treated with a solution of 1.400 g. (0.00316 mole) of 4-carboxybutyltriphenyl phosphonium bromide [E. J. Corey at al., *J. Am. Chem. Soc.*, 91, 5675 (1969)] in 6 ml. of dimethylsulfoxide. To the resulting red solution is added 0.00263 mole of 2-formylmethylcyclopent-2-en-1-one (Example 12) in 2 ml. of dimethylsulfoxide and the mixture is stirred at room temperature for 2.25 hours. The mixture is poured into ice water, sodium hydroxide solution is added to pH 12, and the neutral materials are extracted with diethyl ether. The basic phase is acidified with dilute hydrochloric acid and is extracted with diethyl ether. The organic phase is washed with water and saturated brine, dried ($Na_2SO_4$), and evaporated to a semicrystalline mass. The latter is triturated with hot hexane, the solids are filtered off, and the filtrate is evaporated to yield the subject product as an oil.

EXAMPLE 14

Preparation of 2-(6-carbomethoxy-2-cis-hexenyl)-cyclopent-2-en-1-one

Treatment of 2-(6-carboxy-2-cis-hexenyl)-cyclopent-2-en-1-one (Example 13) with diazomethane in the usual manner is productive of the subject ester.

EXAMPLE 15

Preparation of 1-oxa-2-hydroxy-bicyclo[3.3.0]oct-4-ene

A solution of 6.2 g. (50 mole) of the lactone of cis-2-hydroxycyclopent-4-ene-1-acetic acid [P. A. Grieco, *J. Org. Chem.*, 37, 2363 (1972)] in 350 ml. toluene (dried over molecular sieves) is cooled to −75° C. and treated dropwise under nitrogen with 84 ml. 0.89 M diisobutyl aluminum hydride (10.55 g., 74 mole) over a period of about one hour maintaining the temperature at −74+2° C. The resulting clear solution is stirred at −75° C. for two hours and poured with stirring into a mixture of 15 ml. of concentrated hydrochloric acid and 300 ml. of ice water. The mixture is stirred while warming to room temperature. The layers are separated and the aqueous layer is treated with salt and extracted with three small portions of ether. The combined organic portions are dried over sodium sulfate and evaporated at reduced pressure (75° C. water bath) to yield the product (homogeneous by thin layer of chromatography) as a pale yellow mobile liquid.

EXAMPLE 16

Preparation of 1-hydroxy-2-(6-carboxy-2-dix-hexenyl)cyclopent-3-ene

A solution of the sodium salt of dimethyl sulfoxide is prepared by stirring under nitrogen a mixture of 160 ml. dry dimethyl sulfoxide (dried over molecular sieves and a few pellets of calcium hydride) with 6.0 g. (0.25 mole) of sodium hydride (prepared by making 10.5 g. of 57% sodium hydride dispersion in mineral oil with two 30 mll portions of hexane.) The mixture is warmed with stirring at 75° C. (oil bath) for 2.5 hours.

This solution is added during five minutes to a solution under nitrogen of 44 grams (0.1 mole) of 4-carboxybutyltriphenylphosphonium bromide (Example 18A) in 180 ml. of dry dimethyl sulfoxide. The resulting dark reddish brown solution is stirred for ten minutes, cooled to room temperature and treated with a solution of crude 1-oxa-2-hydroxy-bicyclo[3.3.0]oct-4-ene (6.2 g., 50 mole) (Example 15) in 20 ml. of anhydrous dimethyl sulfoxide. The resulting solution is stirred 16 hours and then treated with 250 ml. ice water.

This brown solution is extracted with two portions of ether to remove neutral material then made strongly acidic with hydrochloric acid. The solution is extracted into four 100 ml. portions of methylene chloride. The combined methylene chloride extracts are mashed with water, then extracted with four 100 ml. portions of 5% sodium bicarbonate. The combined aqueous extracts are mashed with methylene chloride and made acidic to Congo Red with concentrated hydrochloric acid. The mixture is extracted with three 100 ml. portions of methylene chloride. The organic extracts are combined, dried over sodium sulfate and the solvent is evaporated at reduced pressure. The residue (an oily solid) is extracted several times with ether and the ethereal extracts are combined and evaporated at reduced pressure to yield the crude product as a dark oil. The product is purified by chromatograph 6 on silica gel, eluting in the ether. The product is a colorless liquid.

EXAMPLE 17

Preparation of 2-(6-carboxy-2-cis-hexenyl)cyclopent-3-en-1-one

A solution of 3.2 g. (0.5 mole) of 1-hydroxy-2-(6-carboxy-2-cis-hexenyl)cyclopent-3-ene (Example 16) in 60 ml. of reagent acetone is treated dropwise with a total of 6 ml. of 8 N chromic acid in sulfuric acid at 0° C. The oxidation is rather slow. The resulting mixture is dissolved in 200 ml. of water and the solution is extracted with six 50 ml. portions of ether. The combined ethereal extracts are dried over sodium sulfate and the solvent is evaporated at reduced pressure to yield the product as a yellow oil.

EXAMPLE 18

Preparation of 2-(6-carboxy-2-cis-hexenyl)cyclopent-2-en-1-one

A solution of 3 g. of crude 2-(6-carboxy-2-cis-hexenyl)cyclopent-3-en-1-one (Example 17) in 100 ml. of 2% sodium hydroxide is stirred at 80° C. under nitrogen for 1.5 hours. The cooled solution is acidified to Congo Red and extracted with ether. The ethereal extracts are dried over sodium sulfate and evaporated at reduced pressure to afford the product.

EXAMPLE 18A

Preparation of 4-carboxybutyltriphenylphosphonium bromide

A mixture of 103 g. of 5-bromovaleric acid and 152 g. of triphenylphosphine in 400 ml. of acetonitrile is refluxed for 48 hours, cooled, diluted with 100 ml. of benzene and allowed to crystallize. The crystals are filtered, washed with benzene and ether, to yield colorless material, m.p. 207°–209° C.

EXAMPLES 18B–18D

Treatment of the indicated ω-bromoalkanoic acids of Table 3A below with triphenylphosphine by the method described in Example 18A produces the phosphonium bromides of the table.

TABLE 2

| Example | Starting (ω-bromo alkanoic acid | Product phosphonium bromide |
|---|---|---|
| 18B | 4-bromo-n-butyric acid | 3-carboxypropyltriphenylphosphonium |
| 18C | 6-bromo-n-hexanoic acid | 5-carboxypentyltriphenylphosphonium bromide |
| 18D | 7-bromo-n-heptanoic acid | 6-carboxyhexyltriphenylphosphonium bromide |

EXAMPLES 19–21

Treatment of 1-oxa-2-bicyclo[3.3.0]oct-4-ene by the procedure described in Example 16 with the ylids derived from the phosphonium bromides listed in Table 3 below furnishes the product 1-hydroxy-cyclopent-3-enes of the table.

TABLE 3

| Example | Starting phosphonium bromide of Example | Product 1-hydroxy-2-(ω-carboxy-2-cis-alkenyl)cyclopent-3-enes |
|---|---|---|
| 19 | 18B | 1-hydroxy-2-(5-carboxy-2-cis-pentenyl)cyclopent-3-end |
| 20 | 18C | 1-hydroxy-2-(7-carboxy-2-cis-heptenyl)cyclopent-e-end |
| 21 | 18D | 1-hydroxy-2-(8-carboxy-2-cis-octenyl)cyclopent-3-ene |

EXAMPLES 22–24

Oxidation of the 1-hydroxycyclopent-3-enes listed in Table 4 below by the procedure described in Example 17 is productive of the product cyclopent-3-en-1-ones of the table.

TABLE 4

| Example | Starting 1-hydroxycyclopent-3-ene-of Example | Product 2-(ω-carboxy-2-cis-alkenyl)cyclopent-3-en-1-one |
|---|---|---|
| 22 | 19 | 2-(5-carboxy-2-cis-pentenyl)cyclopent-3-en-1-one |
| 23 | 20 | 2-(7-carboxy-2-cis-heptenyl)cyclopent-3-en-1-one |
| 24 | 21 | 2-(8-carboxy-2-cis-octenyl)cyclopent-3-en-1-one |

EXAMPLES 25–27

Base treatment according to the procedure described in Example 18 of the cyclopent-3-ene-1-ones listed in Table 5 below is productive of the product cyclopent-2-en-1-ones of the table.

TABLE 5

| Example | Starting 2-(ω-carboxy-2-cis-alkenyl)cyclopent-3-ene-1-one of Example | Product 2-(ωcarboxy-2-cis-alkenyl(cyclopent-2-en-1-one |
|---|---|---|
| 25 | 22 | 2-(5-carboxy-2-cis-pentenyl)cyclopent-2-en-1-one |
| 26 | 23 | 2-(7-carboxy-2-cis-heptenyl)cyclopent-2-en-1-one |
| 27 | 24 | 2-(8-carboxy-2-cis-octenyl)cyclopent-2-en-1-one |

EXAMPLES 28–30

Treatment of the listed 2-(ω-carboxy-2-cis-alkenyl)-cyclopent-2-en-1-one of Table 6 below with diazomethane in the usual manner is productive of the product methyl esters of the table.

TABLE 6

| Example | Starting carboxylic acid of Example | Product 2-(ω-carbomethoxy-2-cis-alkenyl)cyclopent-2-en-1-one |
|---|---|---|
| 28 | 25 | 2-(5-carbomethoxy-2-cis-pentenyl)cyclopent-2-en- |

TABLE 6-continued

| Example | Starting carboxylic acid of Example | Product 2-(ω-carbomethoxy-2-cis-alkenyl)cyclopent-2-en-1-one |
|---|---|---|
| 29 | 26 | 2-(7-carbomethoxy-2-cis-heptenyl)cyclopent-2-en-1-one |
| 30 | 27 | 2-(8-carbomethoxy-2-cis-octenyl)cyclopent-2-en-1-one |

EXAMPLE 31

Preparation of cyclopentylacetyl chloride

To a solution of 50 g. of cyclopentaneacetic acid containing 2.9 ml. of N,N-dimethylformamide is added dropwise with stirring, 51 g. of thionyl chloride over a period of 15 minutes. After stirring for an additional 60 minutes exces thionyl chloride is removed in vacuo and the residual oil is distilled to give 55.4 g. (97%) of product, b.p. 57°-58° C. (10 mm.).

EXAMPLE 32

Preparation of 1-chloro-4-cyclopentyl-1-trans-buten-3-one

A three-necked flask fitted with a stirrer, a gas inlet tube and a gas outlet tube protected with a calcium chloride tube is surrounded by an ice-water bath. The system is flushed with acetylene for 3 minutes. Carbon tetrachloride (150 ml.) is added to the flask and acetylene is bubbled through at a fast rate for 3 minutes. Aluminum chloride (59 g.) is added and acetylene is bubbled through the mixture for 5 minutes. The gas inlet tube is replaced by a dropping funnel protected by a calcium chloride drying tube. Cyclopentylacetyl chloride (55.4 g., Example 1) is added to the reaction mixture stirring over a period of about 20 minutes. The dropping funnel is replaced by the gas inlet tube and with stirring, acetylene gas is bubbled through at a rate in excess of the saturation rate. After about 15 minutes the rate of absorption of acetylene suddenly becomes very rapid, and the acetylene is passed through as rapidly as it is absorbed. The introduction of acetylene is continued for 45 minutes after the rapid absorption (which lasts about 1 hour) has subsided.

The reaction mixture is poured with stirring into 430 g. of ice and 180 ml. of saturated sodium chloride solution. The aqueous phase is extracted three times with ether. The combined extracts are dried with anhydrous magnesium sulfate and evaporated to dryness in vacuo. After addition of 1.5 g. of hydroquinone the residual oil is distilled to give 57 g. (80%) of oil, b.p. 67°-69° C. (0.14 mm.).

EXAMPLE 33

Preparation of 4-cyclopentyl-1-iodo-1-trans-buten-3-one

A solution of 57 g. of 1-chloro-4-cyclopentyl-trans-buten-3-one (Example 32) in 360 ml. of acetone containing 55 g. of sodium iodide is stirred at the reflux temperature for 18 hours. The resulting mixture is cooled, filtered and and the water liquor is taken to dryness. The residual oil is dissolved in ether washed successively with water, dilute sodium thiosulfate solution, and saturated sodium chloride solution, dried with anhydrous magesium sulfate and taken to dryness to give 87 g. (99%) of orange oil. Vapor phase chromatography shows one peak.

EXAMPLE 34

Preparation of 4-cyclopentyl-1-iodo-1-trans-buten-3-ol

To a solution of 7.1 g. of sodium borohydride in 60 ml. of absolute alcohol, stirred in an ice bath under nitrogen atmosphere, is added dropwise, over a period of about 2 hours, a solution containing 7 g. of 4-cyclopentyl-1-iodo-1-trans-buten-3-one (Example 33) in 160 ml. of absolute alcohol. The temperature is maintained at 5°-10° C. The solution is poured into 850 ml. of iced water and the resulting mixture is extracted three times with ether. The combined extracts are washed with dilute sodium bisulfite solution, saturated sodium chloride solution, dried with anhydrous magnesium sulfate and taken to dryness to give 81 g. of yellow oil. Column chromatography on a column of 1 kg. of silica gel using benzene gives 75 g. (88%) of oily product.

EXAMPLES 35-58

Treatment of the listed carboxylic acids in Table 1 below with thionyl chloride by the procedure disclosed in Example 31 followed by treatment of the resulting acid chloride with acetylene by the procedure described in Example 32, and thence by treatment of the resulting 1-chloro-1-trans-alkene-3-one with sodium iodide by the procedure described in Example 33, and then by treatment of the resulting 1-iodo-1-trans-alkene-3-one with sodium borohydride by the procedure described in Example 34 is productive of the product 3-hydroxy-1-iodo-1-trans-alkenes of the table.

TABLE 1

| Example | Starting Carboxylic acid | Product 3-hydroxy-1-iodo-1-trans-alkene |
|---|---|---|
| 35 | Cyclobutylacetic acid[1] | 4-Cyclobutyl-3-hydroxy-1-iodo-1-trans-butene |
| 36 | 3-Cyclopentyl-propionic acid | 5-Cyclopentyl-3-hydroxy-1-iodo-1-trans-pentene |
| 37 | 4-Cyclopentyl-butyric acid[2] | 6-Cyclopentyl-3-hydroxy-1-iodo-1-trans-hexene |
| 38 | 5-Cyclopentyl-pentanoic acid[2] | 7-Cyclopentyl-3-hydroxy-1-iodo-1-trans-heptene |
| 39 | 6-Cyclopentyl-hexanoic acid[2] | 8-Cyclopentyl-3-hydroxy-1-iodo-1-trans-octene |
| 40 | 2-Methyl-3-cyclopentylpropanoic acid[3] | 5-Cyclopentyl-4-methyl-3-hydroxy-1-iodo-1-trans-pentene |
| 41 | 2-Ethyl-4-cyclopentylbutyric acid[4] | 6-cyclopentyl-4-ethyl-3-hydroxy-1-iodo-1-trans-hexene |
| 42 | (2-trans-methyl-cyclopentyl)-acetic acid[5] | 4-(2-trans-methyl-cyclopentyl)-3-hydroxy-1-iodo-1-trans-butene |
| 43 | 4-(2-trans-methylcyclopentyl)butyric acid[5] | 6-(2-trans-methylcyclopentyl)-3-hydroxy-1-iodo-1-trans-hexene |
| 44 | Cyclohexylacetic acid | 4-Cyclohexyl-3-hydroxy-1-iodo-1-trans-1-trans-butene |
| 45 | 3-Cyclohexyl-propionic acid | 5-cyclohexyl-3-hydroxy-1-iodo-1-trans-pentene |
| 46 | 4-Cyclohexyl-butyric acid[6] | 6-cyclohexyl-3-hydroxy-1-iodo-1-trans-hexene |
| 47 | Cycloheptyl-acetic acid[7] | 4-Cycloheptyl-3-hydroxy-1-iodo-1-trans-butene |
| 48 | (4-methylcycloheptyl)acetic acid[8] | 4-(4-methylcycloheptyl)-3-hydroxy-1-iodo-1-trans-butene |
| 49 | Cyclooctylacetic acid[8,9] | 4-Cyclooctyl-3-hydroxy-1-iodo-1-trans-butene |

TABLE 1-continued

| Example | Starting Carboxylic acid | Product 3-hydroxy-1-iodo-1-trans-alkene |
|---|---|---|
| 50 | (4-methylcyclohexyl)acetic acid[10] | 4-(4-methylcyclohexyl)-3-hydroxy-1-iodo-1-trans-butene |
| 51 | (3-methylcyclohexyl)acetic acid[11] | 4-(3-methylcyclohexyl)-3-hydroxy-1-iodo-1-trans-butene |
| 52 | 3-Cycloheptane carboxylic acid | 3-Cycloheptyl-3-hydroxy-1-iodo-1-trans-propene |
| 53 | Cyclopentane-carboxylic acid | 3-Cyclopentyl-3-hydroxy-1-iodo-1-trans-propene |
| 54 | Trans-2-methylcyclopentane carboxylic acid[12] | 3-(Trans-2-methylcyclopentyl-3-hydroxy-1-iodo-1-trans-propene |
| 55 | all-trans-2,3-dimethylcyclopentane carboxylic acid[13] | 3-(all-trans-2,3-dimethylcyclopentyl)-1-iodo-1-trans-propene |
| 56 | Cyclohexane carboxylic acid | 3-Cyclohexyl-3-hydroxy-1-iodo-1-trans-propene |
| 57 | Trans-4-methylcyclohexane carboxylic acid | 3-(trans-4-methylcyclohexyl)-3-hydroxy-1-iodo-1-trans-propene |
| 58 | Cyclooctane, carboxylic acid[14] | 3-Cyclooctyl-3-hydroxy-1-iodo-1-trans-propene |

[1] C. G. Overberger et al., J. Polymer Sci., Pt. A, 2, 755(1964).
[2] M. I. Goryaev et al., Chem. Abs., 69, 1742, No. 186462 (1968).
[3] C. D. Nenitzescu and G. G. Vantu, Bull. Soc. Chim.
[4] France [5], 2, 2209 (1935). 4G. R. Yohe and R. Adams, J. Amer. Chem. Soc., 50, 1503 (1928).
[5] W. Herz. J. Org. Chem., 20, 1062 (1955).
[6] G. S. Hiers and R. Adams, J. Amer. Chem. Soc., 48, 2385 (1926).
[7] E. E. Royals and A. N. Neal, J. Org. Chem., 21, 1448 (1956).
[8] F. F. Blicke and W. K. Johnson, J. Am. Pharm. Assoc. Sci. Ed., 45, 443 (1956).
[9] L. Ruzicka and H. A. Bockenoogen, Helv. Chim. Acta, 14, 1319 (1931).
[10] A. W. Burgstahler and I. C. Nordin, J. Amer. Chem. Soc., 83, 198 (1961).
[11] J. von Braun and W. Teuffert, Ber., 58B, 2210 (1925).
[12] M. Julia and F. LeGoffic, Bull. Soc. Chim. Fr., 1550 (1965).
[13] V. N. Ipatieff et al., J. Amer. Chem. Soc., 75, 6222 (1953).
[14] A. T. Blomquist and F. W. Sehlaefe, J. Amer. Chem. Soc., 83, 4547 (1961).

EXAMPLE 59

Preparation of 4-cyclopentyl-1-iodo-3-triphenylmethoxy-1-trans-butene

A mixture of 21.4 g. of 4-cyclopentyl-1-iodo-trans-buten-3-ol (Example 34) in 170 ml. of dry pyridine containing 31 g. of triphenylmethyl bromide is heated on the steam bath for 2 hours. The dark mixture is poured into 850 ml. of iced water and the resulting solution is extracted three times with ether. The combind extracts are washed with ice cold 2% hydrochloric acid until the washings are acidic, saturated sodium chloride solution, dried with anhydrous magnesium sulfate and taken to dryness. Trituration of the residue followed by filtration removes triphenylcarbinol. The mother liquor is taken to dryness and the residual syrup is chromatographed on 400 g. of florisil using hexane gives 32 g. (78%) of syrup which solidifies on standing. Recrystallization from hexane affors white crystals, m.p. 87°–88° C.

EXAMPLE 60

Preparation of 4-cyclopentyl-1-iodo-3-(p-methoxyphenyldiphenyl)methoxy-1-trans-butene A solution of 20 g. of 4-cyclopentyl-1-iodo-1-trans-butene-3-ol (Example 34) and 25 g. of p-anisylchlorodiphenylmethane in 170 ml. of dry pyridine is kept at 60° C. for 18 hours, then at 70° C. for 3 hours. The cooled solution is poured into 850 ml. of iced water. The resulting solution is partitioned between ether and water. The ether layer is washed with water, dried with anhydrous magnesium sulfate and taken to dryness. Further evaporation with toluene removes residual pyridine. The resulting oil is chromatographed on 300 g. of fluorisil with hexanes to give 22.3 g. of product. The material is homogeneous according to thin layer chromatography.

EXAMPLES 61–84

Treatment of the listed 3-hydroxy-1-iodo-trans-1-alkenes of Table 2 below with triphenylmethylbromide by the procedure described in Example 59 above is productive of the product 3-triphenylmethoxy-1-iodo-trans-1-alkenes of the table.

TABLE 2

| Example | Starting 3-hydroxy-1-iodo-1-trans-alkene of Example | Product 3-triphenylmethoxy-1-iodo-trans-1-alkene |
|---|---|---|
| 61 | 35 | 4-Cyclobutyl-3-triphenylmethoxy-1-iodo-1-trans-butene |
| 62 | 36 | 5-Cyclopentyl-3-triphenylmethoxy-1-iodo-1-trans-pentene |
| 63 | 37 | 6-Cyclopentyl-3-triphenylmethoxy-1-iodo-1-trans-hexene |
| 64 | 38 | 7-Cyclopentyl-3-triphenylmethoxy-1-iodo-1-trans-heptene |
| 65 | 39 | 8-Cyclopentyl-3-triPhenylmethoxy-1-iodo-1-trans-octene |
| 66 | 40 | 5-Cyclopentyl-4-methyl-3-triphenylmethoxy-1-iodo-1-trans-pentene |
| 67 | 41 | 6-Cyclopentyl-4-ethyl-3-triphenylmethoxy-1-iodo-1-trans-hexene |
| 68 | 42 | 4-(2-trans-methylcyclopentyl)-3-triphenylmethoxy-1-iodo-1-trans-butene |
| 69 | 43 | 6-(2-trans-methylcyclopentyl)-3-triphenylmethoxy-1-iodo-1-trans-hexene |
| 70 | 44 | 4-Cyclohexyl-3-triphenylmethoxy-1-iodo-1-trans-butene |
| 71 | 45 | 5-Cyclohexyl-3-triphenylmethoxy-1-iodo-1-trans-pentene |
| 72 | 46 | 6-Cyclohexyl-3-triphenylmethoxy-1-iodo-1-trans-hexene |
| 73 | 47 | 4-Cycloheptyl-3-triphenylmethoxy-1-iodo-1-trans-butene |
| 74 | 48 | 4-(4-methylcycloheptyl)-3-triphenylmethoxy-1-iodo-1-trans-butene |
| 75 | 49 | 4-Cyclooctyl-3-triphenylmethoxy-1-iodo-1-trans-butene |
| 76 | 50 | 4-(4-methylcyclohexyl)-3-triphenylmethoxy-1-iodo-1-trans-butene |
| 77 | 51 | 4-(3-methylcyclohexyl)-3-triphenylmethoxy-1-iodo-1-trans-butene |
| 78 | 52 | 3-Cycloheptyl-3-triphenylmethoxy-1-iodo-1-trans-propene |
| 79 | 53 | 3-Cyclopentyl-3-triphenylmethoxy-1-iodo-1-trans-propene |

TABLE 2-continued

| Example | Starting 3-hydroxy-1-iodo-1-trans-alkene of Example | Product 3-triphenylmethoxy-1-iodo-trans-1-alkene |
|---|---|---|
| 80 | 54 | 3-(trans-2-methylcyclopentyl)-3-triphenylmethoxy-1-iodo-1-trans-propene |
| 81 | 55 | 3-(all-trans-2,3-dimethylcyclopentyl)-3-triphenylmethoxy-1-iodo-1-trans-propene |
| 82 | 56 | 3-Cyclohexyl-3-triphenylmethoxy-1-iodo-1-trans-propene |
| 83 | 57 | 3-(trans-4-methylcyclohexyl)-3-triphenylmethoxy-1-iodo-1-trans-propene |
| 84 | 58 | 3-Cyclooctyl-3-triphenylmethoxy-1-iodo-1-trans-propene |

EXAMPLE 84A

Preparation of 1,1-dimethyl-cis-3,4-methylenehexane (cis-1-ethyl-2(2,2-dimethoxyethyl)cyclopropane To an ethereal suspension of zinc-silver couple, prepared according to the procedure of J. M. Denis, G. Girard, and J. M. Conia (Synthesis, 1972, 549) from 0.400 g. of silver acetate, 400 ml. of acetic acid, 68 g. of granular zinc, silver wool, and 600 ml. of ether is added dropwise 136 g. of diiodomethane at a rate to maintain a gentle reflux. The mixture is then stirred at room temperature for 1 hour and to it is then added 57.7 g. of 1,1-dimethoxy-cis-3-hexane. [(M. Winter, *Helvetica Chimica Acta*, 46, 1972 (1963)] over a period of 20 minutes and the mixture is refluxed for 5 hours. The mixture is cooled to 0° C., 600 ml. of ether is added followed by 50.5 g. of pyridine dropwise over a period of 1 hour. The resulting precipitate is filtered and washed with ether. The filtrate and washings are combined and evaporated and the residue is fractionally distilled at 12 torr to yield the title compound as a colorless oil.

EXAMPLE 84B

Preparation of cis-3,4-methylene-1-hexanol

To a vigorously stirred solution of 31.6 g. of 1,1-dimethoxy-cis-3,4-methylene-hexane (Example 84A), 75 mg. of hydroquinone, 6 g. of oxalic acid in 150 ml. of acetone heated at 45° C. under an inert atmosphere is added 700 ml. of water over a period of 0.5 hours. The mixture is cooled and extracted well with ether. The organic phase is separated, washed with saturated sodium bicarbonate solution and saturated brine, dried ($Na_2SO_4$) and evaporated. The residue is distilled at 30 torr. to yield the title compound.

EXAMPLE 85

Preparation of cis-5,6-methylene-1-octyn-3-ol

To a solution of 15.2 g. (0.165 mole) of lithium acetylide-ethylenediamine complex in 100 ml. of dry dimethylsulfoxide is added 16.8 g. (0.150 mole) of cis-3,4-methylene-1-hexanol (Example 84B) in 25 ml. of dimethylsulfoxide at a rate to maintain a temperature of 25° C. (cooling). The mixture is then maintained at 25° C. for 2 hours and is poured onto ice and excess hydrochloric acid. The mixture is extracted with ether and the organic phase is washed with water and saturated brine, dried ($Na_2SO_4$), and evaporated to an oil. Distillation in vacuo yields the title compound as a colorless oil.

EXAMPLE 85A

Preparation of 3-triphenylmethoxy-cis-5,6-methylene-1-octyne

A mixture of 13.8 g. of cis-5,6-methylene-1-octyn-3-ol (Example 85) and 33.0 g. of triphenylmethyl bromide in 100 ml. of pyridine is heated to 100° C. for 1.5 hours under an inert atmosphere. The mixture is cooled and filtered. The filtrate is partitioned between ice water and ether. The organic phase is washed with cold dilute hydrochloric acid, saturated sodium bicarbonate solution, and saturated brine, dried ($NaSO_4$), and evaporated to an oil. The latter is dissolved in hexane and passed through 400 g. of Florisil ® to yield after evaporation the title compound as a colorless oil.

EXAMPLE 86

Preparation of 1-iodo-3-triphenylmethoxy-cis-5,6-methylene-trans-1-octene

To 160 ml. of a 0.50 M solution of disiamylborane in diglyme cooled to 0° C. under an inert atmosphere is added 28.6 g. (0.075 mole) 3-triphenylmethoxy-cis-5,6-methylene-1-octyne (Example 85A). The mixture is allowed to come to room temperature and is stirred at ambient temperature for 3 hours. The solution is cooled to 0° C. and 16.9 g. (0.225 mole) of triethylamine oxide is added portionwise such that the temperature is maintained at 0°–5° C. The mixture is stirred at 0° C. for 1 hour and is then poured into 300 ml. of 1 N sodium hydroxide followed immediately by a solution of 57 g. (0.225 mole) of iodine in 150 ml. of tetrahydrofuran. The mixture is stirred at ambient temperatures of 0.5 hour and poured into 1000 ml. of water. The mixture is decolorized by addition of sodium thiosulfate solution and is extracted into ether. The organic phase is washed with water and the solvent is removed in vacuo. The residue is purified by dry-column chromatography upon 1.5 kg. of alumina using hexane as eluent The title compound is obtained as an oil.

EXAMPLES 87–93B

Treatment of the carboxaldehydes listed in Table 3 below with lithium acetylide by the procedure described in Example 85 followed by treatment of the resulting 3-hydroxy-1-alkyne with triphenylmethyl bromide by the procedure of Example 85A furnishes the product 3-triphenylmethoxy-1-alkynes of the table.

TABLE 3

| Example | Starting carboxaldehyde | Product 3-triphenylmethoxy-1-alkynes |
|---|---|---|
| 87 | (2-cyclopentenyl)acetaldehyde[1] | 4-(2-cyclopentenyl)-3-triphenylmethoxy-1-butyne |
| 88 | (2-cyclohexenyl)acetaldehyde[1] | 4-(2-cyclohexenyl)-3-triphenylmethoxy-1-butyne |
| 89 | (3-cyclohexenyl)acetaldehyde[1] | 4-(3-cyclohexenyl)-3-triphenylmethoxy-1-butyne |
| 90 | 1-methyl-1-formylmethylcyclohexane | 1-methyl-1-(3-triphenylmethoxy-1-butyn-yl-4)cyclohexane |
| 91 | adamantane-1-carboxaldehyde | 3-(1-adamantyl)-3-triphenylmethoxy-1-propyne |

TABLE 3-continued

| Ex-ample | Starting carbox-aldehyde | Product 3-triphenyl-methoxy-1-alkynes |
|---|---|---|
| 92 | 2-cyclohexene carboxaldehyde | 3-(2-cyclohexenyl)-3-triphenylmethoxy-1-propyne |
| 93 | 3-cyclohexene carboxaldehyde | 3-(3-cyclohexenyl)-3-triphenylmethoxy-1-propyne |
| 93A | adamantane-2-carboxaldehyde[2] | 3-(2-adamantyl)-3-triphenylmethoxy-1-propyne |
| 93B | (adamantyl-1)-actaldehyde | 4-(1-adamantyl)-3-tri-phenylmethoxy |

References (Table 3)
[1] C. W. Whitehead et al., J. Org. Chem., 26, 2814 (1961).
[2] A. H. Alberts, H. Wynberg and J. Strating, Synthetic Communications, 2, 79 (1972).

EXAMPLES 94-100B

Treatment of the 3-triphenylmethoxy-1-alkynes listed in Table 4 below with disiamylborane, trimethylamine oxide; iodine and aqueous sodium hydroxide by the procedure described in Example 86 furnishes the product 3-triphenylmethoxy-1-iodo-1-trans-alkenes of the table.

Table 4

| Ex-ample | Starting 3-tri-phenylmethoxy-1-alkynes of Example | Product 3-triphenyl-methoxy-1-iodo-1-trans-alkene |
|---|---|---|
| 94 | 87 | 4-(2-cyclopentenyl)-3-triphenylmethoxy-1-iodo-1-trans-butene |
| 95 | 88 | 4-(2-cyclohexenyl)-3-triphenylmethoxy-1-iodo 1-trans-butene |
| 96 | 89 | 4-(3-cyclohexenyl)-3-triphenylmethoxy-1-iodo-1-trans-butene |
| 97 | 90 | 1-methyl-1-(3-triphen-ylmethoxy-1-iodo-trans-1-butenyl-4)cyclo-hexane |
| 98 | 91 | 3-(1-adamantyl)-3-tri-phenylmethoxy-1-iodo-1-trans-propene |
| 99 | 92 | 3-(2-cyclohexenyl)-3-triphenylmethoxy-1-iodo-1-trans-propene |
| 100 | 93 | 3-(3-cyclohexenyl)-3-triphenylmethoxy-1-iodo-1-trans-propene |
| 100A | 93A | 3-(2-adamantyl)-3-tri-phenylmethoxy-1-iodo-1-trans-propene |
| 100B | 93B | 4-(1-adamantyl)-3-tri-phenylmethoxy-1-iodo-1-trans-butene |

EXAMPLE 101

Preparation of methyl 9-oxo-15-hydroxy-17,20-methano-13-trans-prostenoate(11-deoxy-17,20-methanoprostaglandin-E$_1$ methylester)

To a solution of 6.35 g. (12.5 mmoles) of 4-cyclopentyl-1-iodo-3-triphenylmethoxy-1-trans-butene (Example 59) in 15 ml. of dry toluene, cooled to −78° C. in a nitrogen atmosphere, is added dropwise within 10 minutes, 5.4 ml. (12.5 mmoles) of a 2.34 molar solution of n-butyllithium in hexane. The solution is allowed to warm to −40° C. and is maintained at that temperature for 1 hour. The resulting solution containing (3-triphenylmethoxy-4-cyclopentyl-1-trans-butenyl)lithium is cooled to −78° C. and there is added dropwise 5.15 ml. (12.5 mmoles) of a 2.44 molar solution of trimethylaluminum in heptane. The resulting solution containing lithio (3-triphenylmethoxy-4-cyclopentyl-1-trans-butenyl)trimethyl alanate is allowed to warm to −10° C., cooled to −35° C. and there is added dropwise 2.24 g. (10 mmoles) of 2-(6-carbomethoxyhexyl)-2-cyclopentenone (Example 6) in 10 ml. of ether. The 2-phase mixture is then allowed to warm to ambient temperature and is stirred for 18 hours.

The resulting single phase solution is poured cautiously into ice and excess dilute aqueous hydrochloric acid. Ether is added and the organic phase is separated, washed successively with water and saturated sodium chloride solution, dried with anhydrous magnesium sulfate and evaporated to give 8.35 g. methyl 9-oxo-15-triphenylmethoxy-17,20-methano-13-trans-prostenoate as an oil.

The oil is heated under nitrogen atmosphere in 100 ml. of 80% aqueous acetic acid at 80°-85° C. for 1 hour. The resulting solution is take to dryness then evaporated two times with toluene. The resulting oil is triturated with 15 ml. of hexane and filtered to remove triphenylcarbinol (2.5 g., m.p. 156°-158° C.). Evaporation of the mother liquor gives 4.8 g. of viscous oil. The oil, dissolved in 2 ml. of methylene chloride, is applied to a dry column (nylon tube, 1⅜″ flat×36″) containing 360 g. of silica gel. The column (30″ long) is developed with benzene-ethyl acetate (4:1). The first and last 3″ of the column are discarded; the remainder of the column being divided into 1½″ segments. Each of the sixteen segments is triturated with ether, filtered and taken to dryness Segments 1 and 2 give no material. Segments 3, 4 and 5 afford. 512.7 mg. of methyl 9-oxo-15-hydroxy-17,20-methano-13-trans-prostenoate(11-deoxy-17,20-methano-prostaglandin-E$_1$ methyl ester); λmax 2.86 (OH), 5.75 (C═O), and 10.25μ (trans—CH═CH—); thin layer chromatography shows one spot, Rf 0.189. Segments 6 and 7 are combined to give 622 mg. of oil which after partition chromatography affords 193 mg. of methyl 9-oxo-15-epi-hydroxy-17,20-methano-13-trans-prostenoate. (15-epi-11-deoxy-17,20-methylene-prostaglandin-E$_1$ methyl ester); λmax 2.86 (OH), 5.75 (C═O), and 10.25μ (trans—CH═CH—); thin layer chromatography shows one spot, Rf 0.266. There is also obtained an additional 237 mg. of 11-deoxy-17,20-methanolprostaglandin-E$_1$ methyl ester identical in all respects to the material found in segments 3, 4 and 5 above. Segments 8 and 9 are combined to give 850.7 mg. of oil which when further purified by partition chromatography gives 601 mg. of 15-epi-11-deoxy-17,20-methanoprostaglandin-E$_1$, methyl ester identical with the material obtained above.

EXAMPLE 102

Preparation of 9-oxo-15-hydroxy-17,20-methano-13-trans-prostenoic acid(11-deoxy-17,20-methanoprostaglandin-E$_1$)

A suspension of 512.7 mg. of 11-deoxy-17,20-methano prostaglandin-E$_1$ methyl ester (Example 101) in 10 ml. of methanol-water (1:1) containing 200 mg. of potassium hydroxide is stirred under nitrogen atmosphere at 50° C. for 1 hour. The resulting solution is then stirred at ambient temperature for 18 hours. The solution is cooled in an ice-bath, acidified with 1 N hydrochloric acid and extracted several times with ether. The combined extracts are washed with saturated sodium chloride solution, dried with anhydrous magnesium sulfate and taken to dryness to give 481 mg. (98%) of syrup which cyrstallizes on standing.

EXAMPLE 103

Preparation of 9-oxo-15-epi-hydroxy-17,20-methano-13-trans-prostenoic acid(15-epi-11-deoxy-17,20-methanoprostaglandin-$E_1$)

A suspension of 767 mg. of 15-epi-11-deoxy-17,20-methanoprostaglandin $E_1$ (Example 101) in 16 ml. of methanol-water (1:1) containing 300 mg. of potassium hydroxide is treated in the manner described in Example 102 to give 690 mg. (94%) of syrupy product which cyrstallizes on standing.

EXAMPLES 104–134

Treatment of the 3-triphenylmethoxy-1-iodo-1-trans-alkenes listed in Table 5 below with butyl lithium by procedure described in Example 101 above is productive of the 3-triphenylmethoxy 1-trans-alkenyl lithium derivatives of the table.

Table 5

| Example | Starting 3-triphenyl-methoxy-1-iodo-trans-1-alkene of Example | Product 3-triphenylmethoxy-1-trans-alkenyl lithium |
|---|---|---|
| 104 | 61 | 4-Cyclobutyl 3-triphenylmethoxy-1-trans-butenyl lithium |
| 105 | 62 | 5-Cyclopentyl-3-triphenylmethoxy-1-trans-pentenyl lithium |
| 106 | 63 | 6-Cyclopentyl-3-triphenylmethoxy-1-trans-hexenyl lithium |
| 107 | 64 | 7-Cyclopentyl-3-triphenylmethoxy-1-trans-heptenyl lithium |
| 108 | 65 | 8-Cyclopentyl-3-triphenylmethoxy-1-trans-octenyl lithium |
| 109 | 66 | 5-cyclopentyl-4-methyl-3-triphenylmethoxy-1-trans-pentenyl lithium |
| 110 | 67 | 6-cyclopentyl-4-ethyl-3-triphenylmethoxy-1-trans-hexenyl lithium |
| 111 | 68 | 4-(2-trans-methyl cyclopentyl)-3-triphenylmethoxy-1-trans-butenyl lithium |
| 112 | 69 | 6-(2-trans-methylcyclopentyl)-3-triphenylmethoxy-1-trans-hexenyl lithium |
| 113 | 70 | 4-Cyclohexyl-3-triphenylmethoxy-1-trans-butenyl lithium |
| 114 | 71 | 5-Cyclohexyl-3-triphenylmethoxy-1-trans-pentenyl lithium |
| 115 | 72 | 6-Cyclohexyl-3-triphenylmethoxy-1-trans-hexenyl lithium |
| 116 | 73 | 4-Cycloheptyl-3-triphenylmethoxy-1-trans-butenyl lithium |
| 117 | 74 | 4-(4-methylcycloheptyl)-3-triphenylmethoxy-1-trans-butenyl lithium |
| 118 | 75 | 4-Cyclooctyl-3-triphenylmethoxy-1-trans-butenyl lithium |
| 119 | 76 | 4-(4-methylcyclohexyl)-3-triphenylmethoxy-1-trans-butenyl lithium |
| 120 | 77 | 4-(3-methylcyclohexyl)-3-triphenylmethoxy-1-trans-butenyl lithium |
| 121 | 93B | 4-(1-adamantyl)-3-triphenylmethoxy-1-trans-butenyl lithium |
| 122 | 79 | 3-Cyclopentyl-3-triphenylmethoxy-1-trans-propenyl lithium |
| 123 | 80 | 3-(trans-2-methyl-cyclopentyl)-3-triphenylmethoxy-1-trans-propenyl lithium |
| 124 | 81 | 3-(all trans-2,3-dimethylcyclopentyl)-1-trans-propenyl lithium |
| 125 | 82 | 3-Cyclohexyl-3-triphenylmethoxy-1-trans-propenyl lithium |
| 126 | 83 | 3-(trans-4-methylcyclohexyl)-3-triphenylmethoxy-1-trans-propenyl lithium |
| 127 | 84 | 3-Cyclooctyl-3-triphenylmethoxy-1-trans-propenyl lithium |
| 128 | 87 | 4-(2-cyclopenenyl)-3-triphenylmethoxy-1-trans-butenyl lithium |
| 129 | 88 | 4-(2-cyclohexenyl)-3-triphenylmethoxy-1-trans-butenyl lithium |
| 130 | 89 | 4-(3-cyclohexenyl)-3-triphenylmethoxy-1-trans-butenyl lithium |
| 131 | 90 | 1-Methyl-1-(3-triphenylmethoxy-trans-1-butenyl-4)-cyclohexyl lithium |
| 132 | 91 | 3-(1-adamantyl)-3-triphenylmethoxy-1-trans-propenyl lithium |
| 133 | 92 | 3-(2-cyclohexenyl)-3-triphenylmethoxy-1-trans-propenyl lithium |
| 134 | 93 | 3-(3-cyclohexenyl)-3-triphenylmethoxy-1-trans-propenyl lithium |
| 134A | 93A | 3-(2-adamantyl)-3-triphenylmethoxy-1-trans-propenyl lithium |
| 134B | 78 | 3-Cycloheptyl-3-triphenylmethoxy-1-trans-propenyl lithium |

EXAMPLES 135–165

Treatment of the 3-triphenylmethoxy-1-trans-alkenyl lithium derivative listed in Table 6 below with trimethyl aluminum by the procedure described in Example 101 above furnishes of the product lithio (3-triphenylmethoxy-1-trans-alkenyl)trimethyl alanates of the table.

Table 6

| Example | Starting 3-triphenyl-methoxy-1-trans-alkenyl lithium of Example | Product lithio-(triphenylmethoxy-1-trans-alkenyl)-trimethyl alanate |
|---|---|---|
| 135 | 104 | lithio(4-cyclobutyl-3-triphenylmethoxy-1-trans-butenyl)trimethyl |

Table 6 -continued

| Example | Starting 3-triphenyl-methoxy-1-trans-alkenyl lithium of Example | Product lithio-(triphenylmethoxy-1-trans-alkenyl)-trimethyl alanate |
|---|---|---|
| 136 | 105 | lithio(5-cyclopentyl-3-triphenylmethoxy-1-trans-pentenyl)trimethyl alanate |
| 137 | 106 | lithio(6-cyclopentyl-3-triphenylmethoxy-1-trans-hexenyl)trimethyl alanate |
| 138 | 107 | lithio(7-cyclopentyl-3-triphenylmethoxy-1-trans-heptenyl)trimethyl alanate |
| 139 | 108 | lithio(8-cyclopentyl-3-triphenylmethoxy-1-trans-octenyl)trimethyl alanate |
| 140 | 109 | lithio(5-cyclopentyl-4-methyl-3-triphenyl-methoxy-1-trans-pentenyl)trimethyl alanate |
| 141 | 110 | lithio(6-cyclopentyl-4-ethyl-3-triphenyl-methoxy-1-trans-hexenyl)trimethyl alanate |
| 142 | 111 | lithio[4-(2-trans-methylcyclopentyl)-3-triphenylmethoxy-1-trans-butenyl)trimethyl alanate |
| 143 | 112 | lithio[6-1-trans-methylcyclopentyl)-3-triphenylmethoxy-1-trans-hexenyl)tri-methyl alanate |
| 144 | 113 | lithio(4-cyclohexyl-3-triphenylmethoxy-1-trans-butenyl)trimethyl alanate |
| 145 | 114 | lithio(5-cyclohexyl-3-triphenylmethoxy-1-trans-pentenyl)trimethyl alanate |
| 146 | 115 | lithio(6-cyclohexyl-3-triphenylmethoxy-1-trans-hexenyl)trimethyl alanate |
| 147 | 116 | lithio(4-cycloheptyl-3-triphenylmethoxy-1-trans-butenyl)trimethyl alanate |
| 148 | 117 | lithio[4-(4-methylcyclo-heptyl)-3-triphenyl-methoxy-1-trans-butenyl] trimethyl alanate |
| 149 | 118 | lithio(4-cyclooctyl-3-triphenylmethoxy-1-trans-butenyl)tri-methyl alanate |
| 150 | 119 | lithio [4-(4-methyl-cyclohexyl)-3-tri-phenylmethoxy-1-trans-butenyl]trimethyl alanate |
| 151 | 120 | lithio[4-(3-methyl-cyclohexyl)-3-triphen-ylmethoxy-1-trans-butenyl]trimethyl alanate |
| 152 | 121 | lithio[4-(1-adamantyl)-3-triphenylmethoxy-1-trans-butenyl]trimethyl alanate |
| 153 | 122 | lithio(3-cyclopentyl-3-triphenylmethoxy-1-trans-propenyl)trimethyl alanate |
| 154 | 123 | lithio[3-(trans-2-methylcyclopentyl)-3-triphenylmethoxy-1-trans-propenyl]tri-methyl alanate |
| 155 | 124 | lithio[3-(all trans-2,3-dimethylcyclo-pentyl)-3-triphenyl-methoxy-1-trans-propenyl]trimethyl alanate |
| 156 | 125 | lithio(3-cyclohexyl-3-triphenylmethoxy-1-trans-propenyl)tri-methyl alanate |
| 157 | 126 | lithio[3-(trans-4-methylcyclohexyl)-3-triphenylmethoxy-1-trans-propenyl)tri-methyl alanate |
| 158 | 127 | lithio(3-cyclooctyl-3-triphenylmethoxy-1-trans-propenyl)tri-methyl alanate |
| 159 | 128 | lithio[4-(2-cyclopen-enyl)3-triphenyl-methoxy-1-trans-butenyl] trimethyl alanate |
| 160 | 129 | lithio[4-(2-cyclohex-enyl)-3-triphenyl-methoxy-1-trans-buten-yl]trimethyl alanate |
| 161 | 130 | lithio[4-(3-cyclohex-enyl)-3-triphenyl-methoxy-1-trans-buten-yl]trimethyl alanate |
| 162 | 131 | lithio[1-methyl-1-(3-triphenylmethoxy-trans-1-butenyl-4)cyclo-hexyl]trimethyl alanate |
| 163 | 132 | lithio[3-(1-adamantyl)-3-triphenylmethoxy-1-trans-propenyl]tri-methyl alanate |
| 164 | 133 | lithio[3-(2-cyclohex-enyl)-3-triphenyl-methoxy-1-trans-prop-enyl]trimethyl alanate |
| 165 | 134 | lithio[3-(3-cyclohex-enyl)-3-triphenylmeth-oxy-1-trans-propenyl]-trimethyl alanate |
| 165A | 134A | lithio[3-(2-adamantyl)-3-triphenylmethoxy-1-trans-propenyl] trimethyl alanate |
| 165B | 134B | lithio(3-cycloheptyl-3-triphenylmethoxy-1-trans-propenyl]trimeth-yl alanate |

EXAMPLES 166–246

Treatment of the cycloalkenes listed in Table 7 below with the indicated lithio(3-triphenylmethoxy-trans-1-alkenyl)trimethyl alanate is productive, after acid-catalyzed de-O-tritylation of the intermediate alkyl 9-oxo-triphenylmethoxy-13-trans-prostenoates, of the product alkyl 9-oxo-15-hydroxy-13-trans-prostenoates of the table. The entire sequence is carried out by the procedures described in Example 101.

TABLE 7

| Example | Starting Cycloalkenone | Reagent lithio (3-triphenylmethoxy-trans-1-alkenyl)trimethyl alanate of Example | Product alkyl 9-oxo-15-hydrox-13-trans-prostenoates |
|---|---|---|---|
| 166 | 2-(6-carbethoxyhexyl)-cyclopent-2-en-1-one* | 153 | ethyl 9-oxo-15-hydroxy-16,19-methano-20-nor-13-trans-prostenoate |
| 167 | 2-(6-carbethoxyhexyl)-cyclopent-2-en-1-one* | 136 | ethyl 9-oxo-15-hydroxy-18,20-ethano-13-trans-prostenoate |
| 168 | 2-(6-carbethoxyhexyl)-cyclopent-2-en-1-one* | 137 | ethyl 9-oxo-15-hydroxy-19,20-(1,3-propano)-13-trans-prostenoate |
| 169 | 2-(6-carbethoxyhexyl)-cyclopent-2-en-1-one* | 140 | ethyl 9-oxo-15-hydroxy-16-methyl-18,20-ethano-13-trans-prostenoate |
| 170 | 2-(6-carbethoxyhexyl)-cyclopent-2-en-1-one* | 144 | ethyl 9-oxo-15-hydroxy-17,20-ethano-13-trans-prostenoate |
| 171 | 2-(6-carbethoxyhexyl)-cyclopent-2-en-1-one* | 147 | ethyl 9-oxo-15-hydroxy-17,20-(1,3-propano)-13-trans-prostenoate |
| 172 | 2-(6-carbethoxyhexyl)-cyclopent-2-en-1-one* | 150 | ethyl 9-oxo-15-hydroxy-17,20-ethano-20-methyl-13-trans-prostenoate |
| 173 | 2-(6-carbethoxyhexyl)-cyclopent-2-en-1-one* | 152 | ethyl 9-oxo-15-hydroxy-17,18,19,20-tetranor-16-(1-adamantyl)-13-trans-prostenoate |
| 174 | 2-(6-carbo-n-decyloxyhexyl)cyclopent-2-en-1-one (Example 7) | 153 | decyl 9-oxo-15-hydroxy-20-nor-16,19-methano-13-trans-prostenoate |
| 175 | 2-(6-carbethoxyhexyl)-cyclopent-2-en-1-one* | 156 | ethyl 9-oxo-15-hydroxy-16,20-methano-13-trans-prostenoates |
| 176 | 2-(6-carbethoxyhexyl)-cyclopent-2-en-1-one* | 157 | ethyl 9-oxo-15-hydroxy-16,19-ethano-13-trans-prostenoates |
| 177 | 2-(6-carbethoxyhexyl)-cyclopent-2-en-1-one* | 158 | ethyl 9-oxo-15-hydroxy-16,20-(1,3-propano)-13-trans-prostenoate |
| 178 | 2-(6-carbethoxyhexyl)-cyclopent-2-en-1-one* | 159 | ethyl 9-oxo-15-hydroxy-17,20-methano-13-trans,18-prostadienoate |
| 179 | 2-(6-carbethoxyhexyl)-cyclopent-2-en-1-one* | 160 | ethyl 9-oxo-15-hydroxy-17,20-ethano-13-trans,18-prostadienoate |
| 180 | 2-(6-carbethoxyhexyl)-cyclopent-2-en-1-one* | 161 | ethyl 9-oxo-15-hydroxy-17,20-ethano-13-trans,19-prostadienoate |
| 181 | 2-(6-carbethoxyhexyl)-cyclopent-2-en-1-one* | 164 | ethyl 9-oxo-15-hydroxy-16,20-methano-13-trans,17-prostadienoate |
| 182 | 2-(6-carbethoxyhexyl)-cyclopent-2-en-1-one* | 165 | ethyl 9-oxo-15-hydroxy-16,20-methano-13-trans,18-prostadienoate |
| 183 | 2-(6-carbethoxyhexyl)-cyclopent-2-en-1-one* | 163 | ethyl 9-oxo-15-hydroxy-16,17,18,19,20-pentanor-15-(1-adamantyl)-13-trans-prostenoate |
| 184 | 2-(3-carbethoxypropyl)-cyclopent-2-en-1-one* | 138 | ethyl 9-oxo-15,6,7-trinor-15-hydroxy-20,20-(1,4-butano)-13-trans-prostenoate |
| 185 | 2-(4-carbethoxybutyl)-cyclopent-2-en-1-one* | 139 | ethyl 9-oxo-6,7-dinor-15-hydroxy-20-cyclopentyl-13-trans-prostenoate |
| 186 | 2-(8u-carbethoxyoctyl)-cyclopent-2-en-1-one* | 142 | ethyl 9-oxo-7a,7b-bishomo-15-hydroxy-18-methyl-17,20-methano-13-trans-prostenoate |
| 187 | 2-(8-carbethoxyoctyl)-cyclopent-2-en-1-one* | 157 | ethyl 9-oxo-7a,7b-bishomo-15-hydroxy-16,19-ethano-13-trans-prostenoate |
| 188 | 2-(6-carbethoxyhexyl)-cyclohex-2-en-1-one* | 151 | ethyl 9-oxo-10a-homo-15-hydroxy-17,19-(1,3-propano)-13-trans-prostenoate |
| 189 | 2-(7-carbethoxyhexyl)-cyclohex-2-en-1-one* | 152 | ethyl 9-oxo-10a-homo-15-hydroxy-17,18,19-20-tetranor-16-(1-adamantyl)-13-trans-prostenoate |
| 190 | 2-(6-carbethoxyoctyl)-cyclopent-2-en-1-one* | 144 | ethyl 9-oxo-2-ethyl-15-hydroxy-17,20-ethano-13-trans-prostenoate |
| 191 | 2-(6-carbethoxyoctyl)-cyclopent-2-en-1-one* | 159 | ethyl 9-oxo-2-ethyl-15-hydroxy-17,20-methano-13-trans,18-prostadienoate |
| 192 | 2-(6-carbethoxyoctyl)-cyclopent-2-en-1-one* | 165 | ethyl 9-oxo-2-ethyl-15-hydroxy-16,20-methano-13-trans,18-prostadienoate |
| 193 | 2-(6-carbethoxyheptyl)cyclopent-2-en-1-one (Example 3) | 141 | ethyl 9-oxo-2-methyl-15-hydroxy-16-ethyl-19,20-(1,3-propano)-13-trans-prostenoate |
| 194 | 2-(6-carbethoxyheptyl)cyclopent-2-en-1-one (Example 3) | 135 | ethyl 9-oxo-2-methyl-15-hydroxy-17,19-methano-20-nor-13-trans-prostenoate |
| 195 | 2-(6-carbethoxyheptyl)cyclopent-2-en-1-one (Example 3) | 158 | ethyl 9-oxo-2-methyl-15-hydroxy-16,20-(1,3-propano)-13-trans-prostenoate |
| 196 | 2-(6-carbethoxy-5,5-dimethylhexyl)cyclopent-2-en-1-one* | 156 | ethyl 9-oxo-3,3-dimethyl-15-hydroxy-16,20-methano-13-trans-prostenoate |
| 197 | 2-(6-carbethoxy-5,5-dimethylhexyl)cyclopent-2-en-1-one* | 149 | ethyl 9-oxo-3,3-dimethyl-15-hydroxy-17,20-(1,4-butano)-13-trans-prostenoate |
| 198 | 2-(6-carbethoxy-5,5-dimethylhexyl)cyclopent-2-en-1-one* | 165 | ethyl 9-oxo-3,3-dimethyl-15-hydroxy-16,20-methano-13-trans,18-prostadienoate |
| 199 | 2-(6-carbethoxy-5-oxahexyl)cyclopent-2-en-1-one* | 157 | ethyl 9-oxo-3-oxa-15-hydroxy-16,19-ethano-13-trans-prostenoate |

TABLE 7-continued

| Example | Starting Cycloalkenone | Reagent lithio (3-tri-phenylmethoxy-trans-1-alkenyl)trimethyl alanate of Example | Product alkyl 9-oxo-15-hydrox-13-trans-prostenoates |
|---|---|---|---|
| 200 | 2-(6-carbethoxy-5-oxa-hexyl)cyclopent-2-en-1-one* | 152 | ethyl 9-oxo-3-oxa-15-hydroxy-17,18,19,20-tetranor-16-(1-adamantyl)-13-trans-prostenoate |
| 201 | 2-(6-carbethoxy-5-oxa-hexyl)cyclopent-2-en-1-one* | 143 | ethyl 9-oxo-3-oxa-15-hydroxy-20-methyl-19,20-(1,3-propano)-13-trans-prostenoate |
| 202 | 2-(6-carbethoxy-5-oxa-hexyl)cyclopent-2-en-1-one* | 141 | ethyl 9-oxo-3-oxa-15-hydroxy-16-ethyl-19,20-(1,3-propano)-13-trans-prostenoate |
| 203 | 2-(6-carbethoxy-5-oxa-hexyl)cyclopent-2-en-1-one* | 161 | ethyl 9-oxo-3-oxa-15-hydroxy-17,20-ethano-13-trans,19-prostadienoate |
| 204 | 2-(6-carbethoxy-5-thia-hexyl)cyclopent-2-en-1-one* | 165B | ethyl 9-oxo-3-thia-15-hydroxy-16,20-ethano-13-trans-prostenoate |
| 205 | 2-(6-carbethoxy-5-thia-hexyl)cyclopent-2-en-1-one* | 140 | ethyl 9-oxo-3-thia-15-hydroxy-16-methyl-18,20-ethano-13-trans-prostenoate |
| 206 | 2-(6-carbethoxy-5-thia-hexyl)cyclopent-2-en-1-one* | 154 | ethyl 9-oxo-3-thia-15-hydroxy-17-methyl-20-nor-16,19-methano-13-trans-prostenoate |
| 207 | 2-(6-carbethoxy-5-thia-hexyl)cyclopent-2-en-1-one* | 144 | ethyl 9-oxo-3-thia-15-hydroxy-17,20-ethano-13-trans-prostenoate |
| 208 | 2-(6-carbethoxy-6-fluoro-hexyl)cyclopent-2-en-1-one (Example 1) | 148 | ethyl 9-oxo-2-fluoro-15-hydroxy-20-methyl-17,20-(1,3-propano)-13-trans-prostenoate |
| 209 | 2-(6-carbethoxy-6-fluoro-hexyl)cyclopent-2-en-1-one (Example 1) | 165A | ethyl 9-oxo-2-fluoro-15-hydroxy-16,17,18,-19,20-pentanor-15-(2-adamantyl)-13-trans-prostenoate |
| 210 | 2-(6-carbethoxy-6-phenyl-hexyl)cyclopent-2-en-1-one (Example 2) | 156 | ethyl 9-oxo-2-phenyl-15-hydroxy-16,20-methano-13-trans-prostenoate |
| 211 | 2-(6-carbo-n-butoxyhex-yl)cyclopent-2-en-1-one (Example 4) | 165B | butyl 9-oxo-15-hydroxy-16,20-ethano-13-trans-prostenoate |
| 212 | 2-(6-carboisopropoxy-hexyl)cyclopent-2-en-1-one (Example 5) | 165A | isopropyl 9-oxo-15-hydroxy-16,17,18,19,20-pentanor-15-(2-adamantyl)-13-trans-protenoate |
| 213 | 2-(5-carbomethoxy-2-cis-pentnyl)cyclopent-2-en-1-one (Example 28) | 136 | methyl 9-oxo-15-hydroxy-4-nor-18,20-ethano-5-cis,13-trans-prostadienoate |
| 214 | 2-(5-carbomethoxy-2-cis-pentenyl)cyclopent-2-en-1-one (Example 28) | 145 | methyl 9-oxo-15-hydroxy-4-nor-18,20-(1,3-propano)-5-cis,13-trans-prosta-dienoate |
| 215 | 2-(5-carbomethoxy-2-cis-pentyl)cyclopent-2-en-1-one (Example 28) | 164 | methyl 9-oxo-15-hydroxy-4-nor-16,20-methano-5-cis,13-trans,17-protatrienoate |
| 216 | 2-(7-carbomethoxy-2-cis-heptenyl)cyclopent-2-en-1-one (Example 29) | 101 | methyl 9-oxo-15-hydroxy-4a-homo-17,20-methano-5-cis,13-trans-prostadienoate |
| 217 | 2-(7-carbomethoxy-2-cis-heptenyl)cyclopent-2-en-1-one (Example 29) | 163 | methyl 9-oxo-15-hydroxy-4a-homo-16,17,-18,19,20-pentanor-15-(1-adamantyl)-5-cis,13-trans-prostadienoate |
| 218 | 2-(7-carbomethoxy-2-cis-heptenyl)cyclopent-2-en-1-one (Example 29) | 156 | methyl 9-oxo-15-hydroxy-4a-homo-16,20-methano-5-cis,13-trans-prostadienoate |
| 219 | 2-(6-carbomethoxy-2-cis-hexenyl)cyclopent-2-en-1-one (Example 14) | 136 | methyl 9-oxo-15-hydroxy-18,20-ethano-5-cis,13-trans-prostadienoate |
| 220 | 2-(6-carbomethoxy-2-cis-hexenyl)cyclopent-2-en-1-one (Example 14) | 138 | methyl 9-oxo-15-hydroxy-20,20-(1,4-butano)-5-cis,13-trans-prostadienoate |
| 221 | 2-(6-carbomethoxy-2-cis-hexenyl)cyclopent-2-en-1-one (Example 14) | 139 | methyl 9-oxo-15-hydroxy-20-cyclopentyl-cis,13-trans-prostadienoate |
| 222 | 2-(6-carbomethoxy-2-cis-hexenyl)cyclopent-2-en-1-one (Example 14) | 141 | methyl 9-oxo-15-hydroxy-16-ethyl-19,20-(1,3-propano)-5-cis,13-trans-prostadienoate |
| 223 | 2-(6-carbomethoxy-2-cis-hexenyl)cyclopent-2-en-1-one (Example 14) | 144 | methyl 9-oxo-15-hydroxy-17,20-ethano-5-cis,13-trans-prostadienoate |
| 224 | 2-(6-carbomethoxy-2-cis-hexenyl)cyclopent-2-en-1-one (Example 14) | 146 | methyl 9-oxo-15-hydroxy-19,20-(1,4-butano)-5-cis,13-trans-prostadienoate |
| 225 | 2-(6-carbomethoxy-2-cis-hexenyl)cyclopent-2-en-1-one (Example 14) | 147 | methyl 9-oxo-15-hydroxy-17,20-(1,3-propano)-5-cis,13-trans-prostadienoate |
| 226 | 2-(6-carbomethoxy-2- | 150 | methyl 9-oxo-15-hydroxy-20-methyl-17,20- |

TABLE 7-continued

| Example | Starting Cycloalkenone | Reagent lithio (3-triphenylmethoxy-trans-1-alkenyl)trimethyl alanate of Example | Product alkyl 9-oxo-15-hydrox-13-trans-prostenoates |
|---|---|---|---|
|  | cis-hexenyl)cyclopent-2-en-1-one (Example 14) |  | ethano-5-cis,13-trans-prostadienoate |
| 227 | 2-(6-carbomethoxy-2-cis-hexenyl)cyclopent-2-en-1-one (Example 14) | 152 | methyl 9-oxo-15-hydroxy-17,18,19,20-tetranor-16-(1-adamantyl)-5-cis,13-trans-prostadienoate |
| 228 | 2-(6-carbomethoxy-2-cis-hexenyl)cyclopent-2-en-1-one (Example 14) | 155 | methyl 9-oxo-15-hdyroxy-17-methyl-20-nor-16,18-ethano-5-cis,13-trans-prostadienoate |
| 229 | 2-(6-carbomethoxy-2-cis-hexenyl)cyclopent-2-en-1-one (Example 14) | 156 | methyl 9-oxo-15-hydroxy-16,20-methano-5-cis,13-trans-prostadienoate |
| 230 | 2-(6-carbomethoxy-2-cis-hexenyl)cyclopent-2-en-1-one (Example 14) | 101 | methyl 9-oxo-15-hydroxy-17,20-methano-5-cis,13-trans-prostadienoate |
| 231 | 2-(6-carbomethoxy-2-cis-hexenyl)cyclopent-2-en-1-one (Example 14) | 157 | methyl 9-oxo-15-hydroxy-16,19-ethano-5-cis,13-trans-prostadienoate |
| 232 | 2-(6-carbomethoxy-2-cis-hexenyl)cyclopent-2-en-1-one (Example 14) | 158 | methyl 9-oxo-15-hydroxy-16,20-(1,3-propano)-5-cis,13-trans-prostadienoate |
| 233 | 2-(6-carbomethoxy-2-cis-hexenyl)cyclopent-2-en-1-one (Example 14) | 165B | methyl 9-oxo-15-hydroxy-16,20-ethano-5-cis,13-trans-prostadienoate |
| 234 | 2-(6-carbomethoxy-2-cis-hexenyl)cyclopent-2-en-1-one (Example 14) | 163 | methyl 9-oxo-15-hydroxy-16,17,18,19,20-pentanor-15-(1-adamantyl)-5-cis,13-trans-prostadienoate |
| 235 | 2-(6-carbomethoxy-2-cis-hexenyl)cyclopent-2-en-1-one (Example 14) | 165A | methyl 9-oxo-15-hdyroxy-16,17,18,19,20-pentanor-15-(2-adamantyl)-5-cis,13-trans-prostadienoate |
| 236 | 2-(6-carbomethoxy-2-cis-hexenyl)cyclopent-2-en-1-one (Example 14) | 162 | methyl 9-oxo-15-hydroxy-16-methyl-16,20-methano-5-cis,13-trans-prostadienoate |
| 237 | 2-(6-carbomethoxy-2-cis-hexenyl)cyclopent-2-en-1-one (Example 14) | 159 | methyl 9-oxo-15-hydroxy-17,20-methano-5-cis,13-trans,18-prostatrienoate |
| 238 | 2-(6-carbomethoxy-2-cis-hexenyl)cyclopent-2-en-1-one (Example 14) | 160 | methyl 9-oxo-15-hydroxy-17,20-ethano-5-cis,13-trans,18-prostatrienoate |
| 239 | 2-(6-carbomethoxy-2-cis-hexenyl)cyclopent-2-en-1-one (Example 14) | 161 | methyl 9-oxo-15-hydroxy-17,20-ethano-5-cis,13-trans-19-prostatrienoate |
| 240 | 2-(6-carbomethoxy-2-cis-hexenyl)cyclopent-2-en-1-one (Example 14) | 164 | methyl 9-oxo-15-hydroxy-16,20-methano-5-cis,13-trans,17-prostatrienoate |
| 241 | 2-(6-carbomethoxy-2-cis-hexenyl)cyclopent-2-en-1-one (Example 14) | 165 | methyl 9-oxo-15-hydroxy-16,20-methano-5-cis,13-trans-18-prostatrienoate |
| 242 | 2-(8-carbomethoxy-2-cis-octenyl)cyclopent-2-en-1-one (Example 30) | 162 | methyl 9-oxo-15-hydroxy-4a,4b-bishomo-17-methyl-17,20-methano-5-cis,13-trans-prostadienoate |
| 243 | 2-(8-carbomethoxy-2-cis-octenyl)cyclopent-2-en-1-one (Example 30) | 142 | methyl 9-oxo-15-hydroxy-4a,4b-bishomo-18-methyl-17,20-methano-5-cis,13-trans-prostadienoate |
| 244 | 2-(8-carbomethoxy-2-cis-octenyl)cyclopent-2-en-1-one (Example 30) | 165B | methyl 9-oxo-15-hydroxy-4a,4b-bishomo-16,20-ethano-5-cis,13-trans-prostadienoate |
| 245 | 2-(8-carbomethoxy-2-cis-octenyl)cyclopent-2-en-1-one (Example 30) | 151 | methyl 9-oxo-15-hydroxy-4a,4b-bishomo-17,19-(1,3-propano)-5-cis,13-trans-prostadienoate |
| 246 | 2-(8-carbomethoxy-2-cis-octenyl)cyclopent-2-en-1-one (Example 30) | 157 | methyl 9-oxo-15-hydroxy-4a,4b-bishomo-16,19-ethano-5-cis,13-trans-prostadienoate |

EXAMPLES 247–324

Saponification of the alkyl prostenoates listed in Table 8 below by the procedure described in Example 102 furnishes the product prostenoic acids of the table.

TABLE 8

| Example | Starting alkyl prostenoate of Example | Product 9-oxo-15-hydroxy-13-trans-prostenoic acids |
|---|---|---|
| 247 | 166 | 9-oxo-15-hydroxy-16,19-methano-20-nor-13-trans-prostenoic acid |
| 248 | 167 | 9-oxo-15-hydroxy-18,20-ethano-13-trans-prostenoic acid |
| 249 | 168 | 9-oxo-15-hydroxy-19,20-1,3-propano-13-trans-prostenoic acid |

TABLE 8-continued

| Example | Starting alkyl prostenoate of Example | Product 9-oxo-15-hydroxy-13-trans-prostenoic acids |
|---|---|---|
| 250 | 169 | 9-oxo-15-hydroxy-16-methyl-18,20-ethano-13-trans-prostenoic acid |
| 251 | 170 | 9-oxo-15-hydroxy-17,20-ethano-13-trans-prostenoic acid |
| 252 | 171 | 9-oxo-15-hydroxy-17,20-(1,3-propano)-13-trans-prostenoic acid |
| 253 | 172 | 9-oxo-15-hydroxy-17,20-ethano-20-methyl-13-trans-prostenoic acid |
| 254 | 173 | 9-oxo-15-hydroxy-17,18,19,20-tetranor-16-(1-adamantyl)-13-trans-prostenoic acid |
| 255 | 175 | 9-oxo-15-hydroxy-16,20-methano-13-trans-prostenoic acid |
| 256 | 176 | 9-oxo-15-hydroxy-16,19-ethano-13-trans-prostenoic acid |
| 257 | 177 | 9-oxo-15-hydroxy-16,20-(1,3-propano)-13-trans-prostenoic acid |
| 258 | 178 | 9-oxo-15-hydroxy-17,20-methano-13-trans,18-prostadienoic acid |
| 259 | 179 | 9-oxo-15-hydroxy-17,20-ethano-13-trans,18-prostadienoic acid |
| 260 | 180 | 9-oxo-15-hydroxy-17,20-ethano-13-trans,19-prostadienoic acid |
| 261 | 181 | 9-oxo-15-hydroxy-17,20-methano-13-trans,17-prostadienoic acid |
| 262 | 182 | 9-oxo-15-hydroxy-16,20-methano-13-trans,18-prostadienoic acid |
| 263 | 183 | 9-oxo-15-hydroxy-16,17,18,19,20-pentanor-15-(1-adamantyl)-13-trans-prostenoic acid |
| 264 | 184 | 9-oxo-5,6,7-trinor-15-hydroxy-20,20-(1,4-butano)-13-trans-prostenoic acid |
| 265 | 185 | 9-oxo-6,7-dinor-15-hydroxy-20-cyclopentyl-13-trans-prostenoic acid |
| 266 | 186 | 9-oxo-7a,7b-bishomo-15-hydroxy-18-methyl-17,20-methano-13-trans-prostenoic acid |
| 267 | 187 | 9-oxo-7a,7b-bishomo-15-hydroxy-16,19-ethano-13-trans-prostenoic acid |
| 268 | 188 | 9-oxo-10a-homo-15-hydroxy-17,19-(1,3-propano)-13-trans-prostenoic acid |
| 269 | 189 | 9-oxo-10a-homo-15-hydroxy-17,18,19,20-tetra-nor-16-(1-adamantyl)-13-trans-prostenoic acid |
| 270 | 190 | 9-oxo-2-ethyl-15-hydroxy-17,20-ethano-13-trans-prostenoic acid |
| 271 | 191 | 9-oxo-2-ethyl-15-hydroxy-17,20-methano-13-trans,18-prostadienoic acid |
| 272 | 192 | 9-oxo-2-ethyl-15-hydroxy-16,20-methano-13-trans,18-prostadienoic acid |
| 273 | 193 | 9-oxo-2-methyl-15-hydroxy-16-ethyl-19,20-(1,3-propano)-13-trans-prostenoic acid |
| 274 | 194 | 9-oxo-2-methyl-15-hydroxy-17,19-methano-20-nor-13-trans-prostenoic acid |
| 275 | 195 | 9-oxo-2-methyl-15-hydroxy-16,20-(1,3-propano)-13-trans-prostenoic acid |
| 276 | 196 | 9-oxo-3,3-dimethyl-15-hydroxy-16,20-methano-13-trans-prostenoic acid |
| 277 | 197 | 9-oxo-3,3-dimethyl-15-hydroxy-17,20-(1,4-butano)-13-trans-prostenoic acid |
| 278 | 198 | 9-oxo-3,3-dimethyl-15-hydroxy-16,20-methano-13-trans,18-prostadienoic acid |
| 279 | 199 | 9-oxo-3-oxa-15-hydroxy-16,19-ethano-13-trans-prostenoic acid |
| 280 | 200 | 9-oxo-3-oxa-15-hydroxy-17,18,19,20-tetranor-16-(1-adamantyl)-13-trans-prostenoic acid |
| 281 | 201 | 9-oxo-3-oxa-15-hydroxy-20-methyl-19,20-(1,3-propano)-13-trans-prostenoic acid |
| 282 | 202 | 9-oxo-3-oxa-15-hydroxy-16-ethyl-19,20-(1,3-propano)-13-trans-prostenoic acid |
| 283 | 203 | 9-oxo-3-oxa-15-hydroxy-17,20-ethano-13-trans,19-prostadienoic acid |
| 284 | 204 | 9-oxo-3-thia-15-hydroxy-16,20-ethano-13-trans-prostenoic acid |
| 285 | 205 | 9-oxo-3-thia-15-hydroxy-16-methyl-18,20-ethano-13-trans-prostenoic acid |
| 286 | 206 | 9-oxo-3-thia-15-hydroxy-17-methyl-20-nor-16,19-methano-prostenoic acid |
| 287 | 207 | 9-oxo-3-thia-15-hydroxy-17,20-ethano-13-trans-prostenoic acid |
| 288 | 208 | 9-oxo-2-fluoro-15-hydroxy-20-methyl-17,20-(1,3-propano)-13-trans-prostenoic acid |
| 289 | 209 | 9-oxo-2-fluoro-15-hydroxy-16,17,18,19,20-pentanor-15-(2-adamantyl)-13-trans-prostenoic acid |
| 290 | 210 | 9-oxo-2-phenyl-15-hydroxy-16,20-methano-13-trans-prostenoic acid |
| 291 | 213 | 9-oxo-15-hydroxy-4-nor-18,20-ethano-5-cis,13-trans-prostadienoic acid |
| 292 | 214 | 9-oxo-15-hydroxy-4-nor-18,20-(1,3-propano)-5-cis,13-trans-prostadienoic acid |
| 293 | 215 | 9-oxo-15-hydroxy-4-nor-16,20-methano-5-cis,13- |

TABLE 8-continued

| Example | Starting alkyl prostenoate of Example | Product 9-oxo-15-hydroxy-13-trans-prostenoic acids |
|---|---|---|
| | | trans,17-prostatrienoic acid |
| 294 | 216 | 9-oxo-15-hydroxy-4a-homo-17,20-methano-5-cis,13-trans-prostadienoic acid |
| 295 | 217 | 9-oxo-15-hydroxy-4a-homo-16,17,18,19,20-pentanor-15-(1-adamantyl)-5-cis,13-trans-prostadienoic acid |
| 296 | 218 | 9-oxo-15-hydroxy-4a-homo-16,20-methano-5-cis,-13-trans-prostadienoic acid |
| 297 | 219 | 9-oxo-15-hydroxy-18,20-ethano-5-cis,13-trans-prostadienoic acid |
| 298 | 220 | 9-oxo-15-hydroxy-20,20-(1,4-butano)-5-cis,13-trans-prostadienoic |
| 299 | 221 | 9-oxo-15-hydroxy-20-cyclopentyl-5-cis,13-trans-prostadienoic acid |
| 300 | 222 | 9-oxo-15-hydroxy-16-ethyl-19,20-(1,3-propano)-5-cis,13-trans-prostadienoic acid |
| 301 | 223 | 9-oxo-15-hydroxy-17,20-ethano-5-cis,13-trans-prostadienoic acid |
| 302 | 224 | 9-oxo-15-hydroxy-19,20-(1,4-butano)-5-cis,13-trans-prostadienoic acid |
| 303 | 225 | 9-oxo-15-hydroxy-17,20-(1,3-propano)-5-cis,13-trans-prostadienoic acid |
| 304 | 226 | 9-oxo-15-hydroxy-20-methyl-17,20-ethano-5-cis,13-trans-prostadienoic acid |
| 305 | 227 | 9-oxo-15-hydroxy-17,18,-19,20-tetranor-16-(1-adamantyl)-5-cis,13-trans-prostadienoic acid |
| 306 | 228 | 9-oxo-15-hydroxy-17-methyl-20-nor-16,18-ethano-5-cis,13-trans-prostadienoic acid |
| 307 | 229 | 9-oxo-15-hydroxy-16,20-methano-5-cis,13-trans-prostadienoic acid |
| 308 | 230 | 9-oxo-15-hydroxy-17,20-methano-5-cis,13-trans-prostadienoic acid |
| 309 | 231 | 9-oxo-15-hydroxy-16,19-ethano-5-cis,13-trans-prostadienoic acid |
| 310 | 232 | 9-oxo-15-hydroxy-16,20-(1,3-propano)-5-cis,13-trans-prostadienoic acid |
| 311 | 233 | 9-oxo-15-hydroxy-16,20-ethano-5-cis,13-trans-prostadienoic acid |
| 312 | 234 | 9-oxo-15-hydroxy-16,17,-18,19,20-pentanor-15-(1-adamantyl)-5-cis,13-trans-prostadienoic acid |
| 313 | 235 | 9-oxo-15-hydroxy-16,17,-18,19,20-pentanor-15-(2-adamantyl)-5-cis,13-trans-prostadienoic acid |
| 314 | 236 | 9-oxo-15-hydroxy-16-methyl-16,20-methano-5-cis,13-trans-prostadienoic acid |
| 315 | 237 | 9-oxo-15-hydroxy-17,20-methano-5-cis,13-trans,-18-prostatrienoic acid |
| 316 | 238 | 9-oxo-15-hydroxy-17,20-ethano-5-cis,13-trans,18-prostatrienoic acid |
| 317 | 239 | 9-oxo-15-hydroxy-17,20-ethano-5-cis,13-trans,19-prostatrienoic acid |
| 318 | 240 | 9-oxo-15-hydroxy-16,20-methano-5-cis,13-trans,17-prostatrienoic acid |
| 319 | 241 | 9-oxo-15-hydroxy-16,20-methano-5-cis,13-trans,18-prostatrienoic acid |
| 320 | 242 | 9-oxo-15-hydroxy-4a,4b-bishomo-17-methyl-17,-20-methano-5-cis,13-trans-prostadienoic acid |
| 321 | 243 | 9-oxo-15-hydroxy-4a,4b-bishomo-18-methyl-17,-20-methano-5-cis,13-trans-prostadienoic acid |
| 322 | 244 | 9-oxo-15-hydroxy-4a,4b-bishomo-16,20-ethano-5-cis,13-trans-prostadienoic acid |
| 323 | 245 | 9-oxo-15-hydroxy-4a,4b-bishomo-17,19-(1,3-propano)-5-cis,13-trans-prostadienoic acid |
| 324 | 246 | 9-oxo-15-hydroxy-4a,4b-bishomo-16,19-ethano-5-cis,13-trans-prostadienoic acid |

EXAMPLE 325

Preparation of 9α,15-dihydroxy-17,20-methano-13-trans-prostenoic acid

To a solution of 433 mg. of 9-oxo-15-hydroxy-17,20-methano-13-trans-prostenoic acid (Example 102) in 4.5 ml. of tetrahydrofuran, stirred in an ice bath under nitrogen atmosphere, is added dropwise 3.7 ml. of 0.76 M lithium perhydro-9b-boraphenalyl hydride. After 40 minutes at 0° C. there is added 1.62 ml. of 3 N sodium hydroxide followed by 1.62 ml. of 30% hydrogen peroxide. Ether is added and the resulting solution is acidified with 2 N hydrochloric acid. The ether layer is washed several times with saturated sodium chloride solution, dried with anhydrous magnesium sulfate and then to dryness to give the subject product as an oil.

EXAMPLES 326–403

Treatment of the 9-oxo-derivatives designated in Table 9 below with lithium perhydro-9b-boraphenalyl hydride by the procedure described in Example 325 provides the 9α,15- dihydroxy derivatives of the table.

Table 9

| Example | Starting 9-oxo-15-hydroxy-13-trans-prostenoic acid of Example | Product 9-α,15-dihydroxy-13-trans-prostenoic acids |
|---|---|---|
| 326 | 247 | 9α,15-dihydroxy-16,19-methano-20-nor-13-trans-prostenoic acid |
| 327 | 248 | 9α,15-dihydroxy-18,20-ethano-13-trans-prostenoic acid |
| 328 | 249 | 9α,15-dihydroxy-19,20-(1,3-propano)-13-trans-prostenoic acid |
| 329 | 250 | 9α,15-dihyroxy-16-methyl-18,20-ethano-13-trans-prostenoic acid |
| 330 | 251 | 9α,15-dihydroxy-17,20-ethano-13-trans-prostenoic acid |
| 331 | 252 | 9α,15-dihydroxy-17,20-(1,3-propano)-13-trans-prostenoic acid |
| 332 | 253 | 9α,15-dihydroxy-17,20-ethano-20-methyl-13-trans-prostenoic acid |
| 333 | 254 | 9α,15-dihydroxy-17,18,-19,20-tetranor-16-(1-adamantyl)-13-trans-prostenoic acid |
| 334 | 255 | 9α,15-dihydroxy-16,20-methano-13-trans-prostenoic acid |
| 335 | 256 | 9α,15-dihydroxy-16,19-ethano-13-trans-prostenoic acid |
| 336 | 257 | 9α,15-dihydroxy-16,20-(1,3-propano)-13-trans-prostenoic acid |
| 337 | 258 | 9α,15-dihydroxy-17,20-methano-13-trans,18-prostadienoic acid |
| 338 | 259 | 9α,15-dihydroxy-17,20-ethano-13-trans-18-prostadienoic acid |
| 339 | 260 | 9α,15-dihydroxy-17,20-ethano-13-trans,19-prostadienoic acid |
| 340 | 261 | 9α,15-dihydroxy-16,20-methano-13-trans,17-prostadienoic acid |
| 341 | 262 | 9α,15-dihydroxy-16,20-methano-13-trans,18-prostadienoic acid |
| 342 | 263 | 9α,15-dihydroxy-16,17,-18,19,20-pentanor-15-(1-adamantyl)-13-trans-prostenoic acid |
| 343 | 264 | 5,6,7-trinor-9α,15-dihydroxy-20,20-(1,4-buatno)-13-trans-prostenoic acid |
| 344 | 265 | 6,7-dinor-9α,15-dihydroxy-20-cyclopentyl-13-trans-prostenoic acid |
| 345 | 266 | 7a,7b-bishomo-9α,15-dihydroxy-18-methyl-17,20-methano-13-trans-prostenoic acid |
| 346 | 267 | 7a,7b-bishomo-9α,15-dihydroxy-16,19-ethano-13-trans-prostenoic acid |
| 347 | 268 | 10a-homo-9α,15-dihydroxy-17,19-(1,3-propano)-13-trans-prostenoic acid |
| 348 | 269 | 10a-homo-9α,15-dihydroxy-17,18,19,20-tetranor-16-(1-adamantyl)-13-trans-prostenoic acid |
| 349 | 270 | 2-ethyl-9α,15-dihydroxy-17,20-ethano-13-trans-prostenoic acid |
| 350 | 271 | 2-ethyl-9α,15-dihydroxy-17,20-methano-13-trans,18-prostadienoic acid |
| 351 | 272 | 2-ethyl-9α,15-dihydroxy-16,20-methano-13-trans,18-prostadienoic acid |
| 352 | 273 | 2-methyl-9α,15-dihydroxy-16-ethyl-19,20-(1,3-propano)-13-trans-prostenoic acid |
| 353 | 274 | 2-methyl-9α,15-dihydroxy-17,19-methano-20-nor-13-trans-prostenoic acid |
| 354 | 275 | 2-methyl-9α,15-dihydroxy-16,20-(1,3-propano)-13-trans-prostenoic acid |
| 355 | 276 | 3,3-dimethyl-9α,15dihydroxy-16,20-methano-13-trans-prostenoic acid |
| 356 | 277 | 3,3-dimethyl-9α,15-dihydroxy-17,20-(1,4-butano)-13-trans-prostenoic acid |
| 357 | 278 | 3,3-dimethyl-9α,15-dihydroxy-16,20-methano-13-trans,18-prostadienoic acid |
| 358 | 279 | 3-oxa-9α,15-dihydroxy-16,19-ethano-13-trans-prostenoic acid |
| 359 | 280 | 3-oxa-9α,15-dihydroxy-17,18,19,20-tetranor-16-(1-adamantyl)-13-trans-prostenoic acid |
| 360 | 281 | 3-oxa-9α,15-dihydroxy-20-methyl-19,20-(1,3-propano)-13-trans-prostenoic acid |
| 361 | 282 | 3-oxa-9α,15-dihydroxy-16-ethyl-19,20-(1,3-propano)-13-trans-prostenoic acid |
| 362 | 283 | 3-oxa-9α,15-dihydroxy-17,20-ethano-13-trans,-19-prostadienoic acid |
| 363 | 284 | 3-thia-9α,15-dihydroxy-16,20-ethano-13-trans-prostenoic acid |
| 364 | 285 | 3-thia-9α,15-dihydroxy-16-methyl-18,20-ethano-13-trans-prostenoic acid |
| 365 | 285 | 3-thia-9α,15-dihydroxy-17-methyl-20-nor-16,19-methano-13-trans-prostenoic acid |
| 366 | 287 | 3-thia-9α,15-dihydroxy-17,20-ethano-13-trans-prostenoic acid |
| 367 | 288 | 2-fluoro-9α,15-dihydroxy-20-methyl-17,-20-(1,3-propano)-13-trans-prostenoic acid |
| 368 | 289 | 2-fluoro-16,17,18,19,-20-pentanor-15-(2-adamantyl)-13-trans-prostenoic acid |
| 369 | 290 | 2-phenyl-9α,15-dihydroxy-16,20-methano-13-trans-prostenoic |

Table 9-continued

| Example | Starting 9-oxo-15-hydroxy-13-trans-prostenoic acid of Example | Product 9-α,15-dihydroxy-13-trans-prostenoic acids |
|---|---|---|
| 370 | 291 | 9α,15-dihydroxy-4-nor-18,20-ethano-5-cis, 13-trans-prostadienoic acid |
| 371 | 292 | 9α,15-dihydroxy-4-nor-18,20-(1,3-propano)-5-cis,13-trans-prostadienoic acid |
| 372 | 293 | 9α,15-dihydroxy-4-nor-16,20-methano-5-cis,13-trans,17-prostatrienoic acid |
| 373 | 294 | 9α,15-dihydroxy-4a-homo-17,20-methano-5-cis,13-trans-prostadienoic acid |
| 374 | 295 | 9α,15-dihydroxy-4a-homo-16,17,18,19,20-pentanor-15(1-adamantyl)-5-cis,13-trans-prostadienoic acid |
| 375 | 296 | 9α,15-dihydroxy-4a-homo-16,20-methano-5-cis,13-trans-prostadienoic acid |
| 375a | 103 | 9α,15-epi-dihydroxy-17,20-methano-13-trans-prostenoic acid |
| 376 | 297 | 9α,15-dihydroxy-18,20-ethano-5-cis,13-trans-prostadienoic acid |
| 377 | 298 | 9α,15-dihydroxy-20,20-(1,4-butano)-5-cis,13-trans-prostadienoic acid |
| 378 | 299 | 9α,15-dihydroxy-20-cyclopentyl-5-cis,13-trans-prostadienoic acid |
| 379 | 300 | 9α,15-dihydroxy-16-ethyl-19,20-(1,3-propano)-5-cis,13-trans-prostadienoic acid |
| 380 | 301 | 9α,15-dihydroxy-17,20-ethano-5-cis,13-trans-prostadienoic acid |
| 381 | 302 | 9α,15-dihydroxy-19,20-(1,4-butano)-5-cis,13-trans-prostadienoic acid |
| 382 | 303 | 9α,15-dihydroxy-17,20-(1,3-propano)-5-cis,13-trans-prostadienoic acid |
| 383 | 304 | 9α,15-dihydroxy-20-methyl-17,20-ethano-5-cis,13-trans-prostadienoic acid |
| 384 | 305 | 9α,15-dihydroxy-17,18,19,20-tetranor-16-(1-adamantyl)-5-cis,13-trans-prostadienoic acid |
| 385 | 306 | 9α,15-dihydroxy-17-methyl-20-nor-16,18-ethano-5-cis,13-trans-prostadienoic acid |
| 386 | 307 | 9α,15-dihydroxy-16,20-methano-5-cis,13-trans-prostadienoic acid |
| 387 | 308 | 9α,15-dihydroxy-17,20-methano-5-cis,13-trans-prostadienoic acid |
| 388 | 309 | 9α,15-dihydroxy-16,19-ethano-5-cis,13-trans-prostadienoic acid |
| 389 | 310 | 9α,15-dihydroxy-16,20-(1,3-propano)-5-cis,13-trans-prostadienoic acid |
| 390 | 311 | 9α,15-dihydroxy-16,20-ethano-5-cis,13-trans-prostadienoic acid |
| 391 | 312 | 9α,15-dihydroxy-16,17,18,19,20-pentanor-15-(1-adamantyl)-5-cis,13-trans-prostenoic acid |
| 392 | 313 | 9α,15-dihydroxy-16,17,18,19,20-pentanor-15-(2-adamantyl-5-cis,13-trans-prostadienoic acid |
| 393 | 314 | 9α,15-dihydroxy-16-methyl-16,20-methano-5-cis,13-trans-prostadienoic acid |
| 394 | 315 | 9α,15-dihydroxy-17,20-methano-5-cis,13-trans-18-prostatrienoic acid |
| 395 | 316 | 9α,15-dihydroxy-17,20-ethano-5-cis,13-trans-18-prostatrienoic acid |
| 396 | 317 | 9α,15-dihydroxy-17,20-ethano-5-cis,13-trans-19-prostatrienoic acid |
| 397 | 318 | 9α,15-dihydroxy-16,20-methano-5-cis,13-trans-17-prostatrienoic acid |
| 398 | 319 | 9α,15-dihydroxy-16,20-methanao-5-cis,13-trans-18-prostatrienoic acid |
| 399 | 320 | 9α,15-dihydroxy-4a,4b-bishomo-17-methyl-17,20-methano-5-cis,13-trans-prostadienoic acid |
| 400 | 321 | 9α,15-dihydroxy-4a,4b-bishomo-18-methyl-17,20-methano-5-cis,13-trans-prostadienoic acid |
| 401 | 322 | 9α,15-dihydroxy-4a,4b-bishomo-16,20-ethano-5-cis,13-trans-prostadienoic acid |
| 402 | 323 | 9α,15-dihydroxy-4a,4b-bishomo-17,19-(1,3-propano)-5-cis,13-trans-prostadienoic acid |
| 403 | 324 | 9α,15-dihydroxy-4a,4b-bishomo-16,19-ethano-5-cis,13-trans-prostadienoic acid |

EXAMPLE 404

Preparation of 9α/9β,15-dihydroxy-16,19-methano-20-nor-13-trans-prostenoic acid

To a stirred, ice-cold solution of 355 mg. (1.00 mmoles) of 9-oxo-15-hydroxy-16,19-methano-20-nor-13-trans-prostenoic acid (Example 166) in 50 ml. of ethanol is added 409 mg. (10.8 mmoles) of sodium borohydride in small portions during 1 minute. The mixture is protected from moisture and is stirred at 0° C. for 5 minutes and at ambient temperature for 6 hours. The bulk of the ethanol is evaporated at room temperature, and the residue is treated with ether followed by dilute hydrochloric acid while cooling in an ice bath. The organic phase is separated and washed with water and saturated sodium chloride solution. The solution is dried over magnesium sulfate and concentrated. The residue is purified by preparative thin layer chromatography on silica gel to give an oil, $\lambda$ max 3310 (hydroxyl groups), 1705 (acid carbonyl group), and 970 cm$^{-1}$ (trans vinyl group).

EXAMPLE 405-411

Treatment of the 9-oxo derivatives listed in Table 10 below with sodium borohydride in accordance with the procedure described in Example 404 is productive of the 9-hydroxy derivatives of the table. Each of these derivatives represents a mixture of 9α- and 9β-hydroxy compounds.

Table 10

| Example | Starting 9-oxo-13-trans-prostenoic acid of Example | Product 9α/β,-15-dihydroxy-13-trans-prostenoic acids |
|---|---|---|
| 405 | 251 | 9α/β,15-dihydroxy-17,20-ethano-3-trans-prostenoic acid |
| 406 | 253 | 9α/β,15-dihydroxy-17,20-ethano-20-methyl-13-trans-prostenoic acid |
| 407 | 256 | 9α/β,15-dihydroxy-16,19-ethano-20-methyl-13-trans-prostenoic acid |
| 408 | 261 | 9α/β,15-dihydroxy-16,20-methano-13-trans,17-prostadienoic acid |
| 409 | 262 | 9α/β,15-dihydroxy-16,20-methano-13-trans,18-prostadienoic acid |
| 410 | 267 | 9α/β,15-dihydroxy-7a,7b-bishomo-16,19-ethano-13-trans-prostenoic acid |
| 411 | 314 | 9α/β,15-dihydroxy-16-methyl-16,20-methano-5-cis,13-trans-prostadienoic acid |

EXAMPLE 412

Preparation of
9-oxo-15-hydroxy-15-methyl-20,20-(1,4-butano)-5-cis,13-trans-prostadienoic acid and
9α,15-dihydroxy-15-methyl-20,20-(1,4-butano)-5-cis,13-trans-prostadienoic acid A solution of methyl 9-oxo-15-hydroxy-20,20(1,4-butano)-5-cis,13-trans-prostadienoate (Example 220) in tetrahydrofuran is added to 1.1 equivalent of lithium perhydro-9b-boraphenalyl hydride in tetrahydrofuran at −78° C. After 30 minutes equal volumes of 5% aqueous sodium carbonate and 30% aqueous hydrogen peroxide is added, and the solution is stirred 15 minutes. The solution is diluted with water and extracted with ether. The organic phase is dried (magnesium sulfate) and concentrated in vacuo to give methyl 9α,15-dihydroxy-20,20-(1,4-butano)-5-cis,13-trans-prostadienoate, contaminated with methyl 9β, 15α-dihydroxy-5-cis,13-trans,17-cis-prostatienoate. The crude mixture of esters is dissolved in methylene chloride and added to a refluxing solution of 1.2 equivalents of 2,3-dichloro-5,6-dicyanobenzoquinone (DDQ) in methylene chloride. After 5 hours, the solution is cooled and filtered. The filtrate is diluted with two volumes of ether, extracted with 5% aqueous sodium carbonate and dried with magnesium sulfate. The solution is concentrated in vacuo to give methyl 9α-hydroxy-15-oxo-20,20-(1,4-butano-5-cis-13-trans-prostadienoate and 9β-hydroxy-15-oxo-20,20-(1,4-butano-5-cis,13-trans-prostadienoate. The crude material is dissolved in benzene and 1.2 equivalents each of triethylamine and trimethylsilyl chloride is added. The triethylamine hydrochloride is removed by filtration and the solution is concentrated in vacuo to give methyl 9α-trimethylsiloxy-15-oxo-20,20-(1,4-butano)-5-cis,13-trans-prostadienoate and the corresponding 9β-trimethylsiloxy derivative.

The siloxy derivatives are dissolved in ether at 0° C. and 1.05 equivalents of methyl magnesium bromide in ether is added. After the reaction is complete, the solution is poured into saturated aqueous ammonium chloride and extracted with ether. The ether is dried and concentrated in vacuo to give methyl 9α-trimethylsiloxy-15α-hydroxy-15β-methyl-20,20-(1,4-butano)-5-cis,13-trans-prostadienoate, and methyl 9α-trimethylsiloxy-15β-hydroxy-15α-methyl-20,20-(1,4-butano)-5-cis,13-trans-prostadienoate, methyl 9β-trimethylsiloxy-15α-hydroxy-15β-methyl-20,20-(1,4-butano-5-cis,13-trans-prostadienoate, and methyl 9β-trimethylsiloxy-15β-hydroxy-15α-methyl-20,20-(1,4-butano)-5-cis,13-trans-prostadienoate. Hydrolysis of the siloxy functions of each in a solution of methanol water and acetic and gives methyl 9α,15α-dihydroxy-15β-methyl-20,20-(1,4-butano)-5-cis,13-trans-prostadienoate, methyl 9α,15β-dihydroxy-15α-methyl-20,20-(1,4-butano)-5-cis,13-trans-prostadienoate, methyl 9β,15α-dihydroxy-15β-methyl-20,20-(1,4-butano)-5-cis,13-trans-prostadienoate and methyl 9β15β-dihydroxy-15α-methyl-20,20-(1,4-butano)-5-cis,13-trans-prostadienoate, which are separated by dry column chromatography and further purified by partition chromatography. Saponification (method of Example 102) of each component in 50% aqueous methanol with potassium hydroxide gives the corresponding free acids.

Treatment of a solution of methyl 9α,15α-dihydroxy-15β-methyl-20,20-(1,4-butano)-5-cis,13-trans-prostadienoate in methylene chloride with Collins reagent gives methyl 9-oxo-15α-hydroxy-15β-methyl-20,20-(1,4-butano)-5-cis,13-trans-prostadienoate, saponification of which (method of Example 102) gives 9-oxo-15α-hydroxy-15β-methyl-20,20-(1,4-butano)-5-cis,13-trans-prostadienoic acid.

Similar treatment of the 15β-hydroxy esters gives methyl 9-oxo-15β-hydroxy-15α-methyl-20,20-(1,4-butano)-5-cis-13-trans-prostadienoate which gives 9-oxo-15β-hydroxy-15α-methyl-20,20-(1,4-butano)-5-cis,13-trans-prostadienoic acid after saponification.

EXAMPLES 413-446P

Treatment of the 9-oxo-15-hydroxy prostenoic esters of Table 11 below by the sequence of reactions described in Example 412 is productive of the 9α,15-dihydroxy-15-methyl and the 9-oxo-15-hydroxy-15-methyl products of the table. Also prepared in the course of these reaction sequences are the ethyl or methyl esters corresponding to the products of the table, the 9β-hydroxy derivatives corresponding to the listed 9α-hydroxy derivatives and their ethyl or methyl esters, the 15-keto derivatives of the 9α- and 9β-hydroxy compounds corresponding to the 9-oxo starting compounds, and the 9α- or 9β-trimethyl-silyloxy ethyl esters of the 15-keto and 15-hydroxy-15-methyl compounds. In all cases both the 15α-hydroxy-15β-methyl and the 15β-hydroxy-15α-methyl products and intermediates are obtained. These are separable by chromatographic procedures.

TABLE II

| Example | Starting 9-oxo-15-hydroxy-13-trans-prostenoate of Example | Product 15-hydroxy-15-methyl derivatives |
|---|---|---|
| 413 | 167 | 9-oxo-15-hydroxy-15-methyl-18,20-ethano-13-trans-prostenoic acid and 9α,15-dihydroxy-15-methyl-18,20-ethano-13-trans-prostenoic acid |
| 414 | 168 | 9-oxo-15-hydroxy-15-methyl-19,20-(1,3-propano)-13-trans-prostenoic acid and 9α,15-dihydroxy-15-methyl-19,20-(1,3-propano)-13-trans-prostenoic acid |
| 415 | 170 | 9-oxo-15-hydroxy-15-methyl-17,20-ethano-13-trans-prostenoic acid and 9α,15-dihydroxy-15-methyl-17,20-ethano-13-trans-prostenoic acid |
| 416 | 171 | 9-oxo-15-hydroxy-15-methyl-17,20-(1,3-propano)-13-trans-prostenoic acid and 9α,15-dihydroxy-15-methyl-17,20-(1,3-propano)-13-trans-prostenoic acid |
| 417 | 172 | 9-oxo-15-hydroxy-15-methyl-17,20-ethano-20-methyl-13-trans-prostenoic acid and 9α,15-dihydroxy-15-methyl-17,20-ethano-20-methyl-13-trans-prostenoic acid |
| 418 | 175 | 9-oxo-15-hydroxy-15-methyl-16,20-methano-13-trans-prostenoic acid and 9α,15-dihydroxy-15-methyl-16,20-methano-13-trans-prostenoic acid |
| 419 | 178 | 9-oxo-15-hydroxy-15-methyl-17,20-methano-13-trans,18-prostadienoic acid and 9α,15-dihydroxy-15-methyl-17,20-methano-13-trans,18-prostadienoic acid |
| 420 | 179 | 9-oxo-15-hydroxy-15-methyl-17,20-ethano-13-trans,18-prostadienoic acid and 9α,15-dihydroxy-15-methyl-17,20-ethano-13-trans,18-prostadienoic acid |
| 421 | 180 | 9-oxo-15-hydroxy-15-methyl-17,20-ethano-13-trans,19-prostadienoic acid and 9α,15-dihydroxy-15-methyl-17,20-ethano-13-trans,19-prostadienoic acid |
| 422 | 184 | 9-oxo-5,6,7-trinor-15-hydroxy-15-methyl-20,20-(1,4-butano)-13-trans-prostenoic acid and 5,6,7-trinor-9α,15-dihydroxy-15-methyl-20,20-(1-)butano)-13-trans-prostenoic acid |
| 423 | 185 | 9-oxo-6,7-dinor-15-hydroxy-15-methyl-20-cyclopentyl-13-trans-prostenoic acid and 6,7-dinor-9α,15-dihydroxy-15-methyl-20-cyclopentyl-13-trans-prostenoic acid |
| 424 | 186 | 9-oxo-7a,7b-bishomo-15-hydroxy-15-methyl-18-methyl-17,20-methano-13-trans-prostenoic acid and 7a,7b-bishomo-9α,15-dihydroxy-15-methyl-18-methyl)-17,20-ethano-13-trans-prostenoic acid |
| 425 | 188 | 9-oxo-10a-homo-15-hydroxy-15-methyl-17,19-(1,3-propano)-13-trans-prostenoic acid and 10a-homo-9α,15-dihydroxy-15-methyl-17,19-(1,3-propano)-13-trans-prostenoic acid |
| 426 | 190 | 9-oxo-2-ethyl-15-hydroxy-15-methyl-17,20-ethano-13-trans-prostenoic acid and 2-ethyl-9α,15-dihydroxy-15-methyl-17,20-ethano-13-trans-prostenoic acid |
| 427 | 191 | 9-oxo-2-ethyl-15-hydroxy-15-methyl-17,20-methano-13-trans,18-prostadienoic acid and 2-ethyl-9α,15-dihydroxy-15-methyl-17,20-methano-13-trans,18-prostadienoic acid |
| 428 | 194 | 9-oxo-2-methyl-15-hydroxy-15-methyl-17,19-methano-20-nor-13-trans-prostenoic acid and 2-methyl-9α,15-dihydroxy-15-methyl-17,20-metha-20-nor-13-trans-prostenoic acid |
| 429 | 197 | 9-oxo-3,3-dimethyl-15-hydroxy-15-methyl-17,20-(1,4-butano)-13-trans-prostenoic acid and 3,3-dimethyl-9α,15-dihydroxy-15-methyl-17,20-(1,4-butano)-13-trans-prostenoic acid |
| 430 | 201 | 9-oxo-3-oxa-15-hydroxy-15-methyl-20-methyl-19,20-(1,3-propano)-13-trans-prostenoic acid and 3-oxa-9α,15-dihydroxy-15-methyl-20-methyl-19,20-(1,3-propano)-13-trans-prostenoic acid |
| 431 | 203 | 9-oxo-3-oxa-15-hyrroxy-15-methyl-17,20-ethano-13-trans,19-prostadienoic acid and 3-oxa-9α,15-dihydroxy-15-methyl-17,20-ethano-13-trans,19-prostadienoic acid |
| 432 | 207 | 9-oxo-3-thia-15-hydroxy-15-methyl-17,20-ethano-13-trans-prostenoic acid and 3-thia-9α,15-dihydroxy-15-methyl-17,20-ethano-13-trans-prostenoic acid |
| 433 | 208 | 9-oxo-2-fluoro-15-hydroxy-15-methyl-20-methyl-17,20-(1,3-propano)-15-trans-prostenoic acid and 2-fluoro-9α,15-dihydroxy-15-methyl-20-methyl-17,20-(1,3-propano)-13-trans-prostenoic acid |
| 434 | 213 | 9-oxo-15-hydroxy-15-methyl-4-nor-18,20-ethano-5-cis,13-trans-prostadienoic acid and 9α,15-dihydroxy-15-methyl-4-nor-18,20-ethano-5-cis,-13-trans-prostadienoic acid |
| 435 | 214 | 9-oxo-15-hydroxy-15-methyl-4-nor-18,20-(1,3-propano)-5-cis,13-trans-prostadienoic acid and 9α,15-dihydroxy-15-methyl-4-nor-18,20-(1,3-propano)-5-cis,13-trans-prostadienoic acid |
| 436 | 216 | 9-oxo-15-hydroxy-15-methyl-4a-homo-17,20-methano-5-cis,13-trans-prostdienoic acid and 9α,15-dihydroxy-15-methyl-4a-homo-17,20-methano-5-cis,-13-trans-prostadienoic acid |
| 437 | 219 | 9-oxo-15-hydroxy-15-methyl-18,20-ethano-5-cis,13-trans-prostadienoic acid and 9α,15-dihydroxy-15-methyl-18,20-ethano-5-cis,13-trans-prostadienoic acid |
| 438 | 221 | 9-oxo-15-hydroxy-15-methyl-20-cyclopentyl-5-cis,13-trans-prostadienoic acid and 9α,15-dihydroxy-15-methyl-20-cyclopentyl-5-cis,13-trans-prostadienoic acid |
| 439 | 224 | 9-oxo-15-hydroxy-15-methyl-19,20-(1,4-butano)-5-cis,13-trans-prostadienoic acid and 9α,15-dihydroxy-15-methyl-19,20-(1,4-butano)-5-cis,13-trans-prostadienoic acid |
| 440 | 226 | 9-oxo-15-hydroxy-15-methyl-20-methyl-17,20-ethano-5-cis,13-trans- |

TABLE II-continued

| Example | Starting 9-oxo-15-hydroxy-13-trans-prostenoate of Example | Product 15-hydroxy-15-methyl derivatives |
|---|---|---|
| | | prostadienoic acid and 9α,15-dihydroxy-15-methyl-20-methyl-17,20-ethano-5-cis,13-trans-prostadienoic acid |
| 441 | 230 | 9-oxo-15-hydroxy-15-methyl-17,20-methano-5-cis,13-trans-prostadienoic acid and 9α,15-dihydroxy-15-methyl-17,20-methano-5-cis,13-trans-prostadienoic acid |
| 442 | 237 | 9-oxo-15-hydroxy-15-methyl-17,20-methano-5-cis,13-trans,18-prostatrienoic acid and 9α,15-dihydroxy-15-methyl-17,20-methano-5-cis,13-trans,18-prostatrienoic acid |
| 443 | 238 | 9-oxo-15-hydroxy-15-methyl-17,20-ethano-5-cis,13-trans,18-prostatrienoic acid and 9α,15-dihydroxy-15-methyl-17,20-ethano-5-cis,13-trans,18-prostatrienoic acid |
| 444 | 239 | 9-oxo-15-hydroxy-15-methyl-17,20-ethano-5-cis,13-trans,19-prostatrienoic acid and 9α,15-dihydroxy-15-methyl-17,20-ethano-5-cis,13-trans,19-prostatrienoic acid |
| 445 | 243 | 9-oxo-15-hydroxy-15-methyl-4a,4b-bishomo-18-methyl-17,20-methano-5-cis,13-trans-prostadienoic acid and 9α,15-dihydroxy-15-methyl-4a,4b-bishomo-18-methyl-17,20-methano-5-cis,13-trans-prostadienoic acid |
| 446 | 245 | 9-oxo-15-hydroxy-15-methyl-4a,4b-bishomo-17,19-(1,3-propano)-5-cis-13-trans-prostadienoic acid and 9α,15-dihydroxy-15-methyl-4a,4b-bishomo-17,19-(1,3-propano)-5-cis,13-trans-prostadienoic acid |
| 446A | 544 | 9-oxo-15-hydroxy-15-methyl-cis-17,18-methano-13-trans-prostenoic acid and 9α,15-dihydroxy-15-methyl-cis-17,18-methano-13-trans-prostenoic acid |
| 446B | 546 | 9-oxo-6,7-dinor-15-hydroxy-15-methyl-cis-17,18-methano-13-trans-prostenoic acid and 9α,15-dihydroxy-6,7-dinor-15-methyl-cis,17,18-methano-13-trans-prostenoic acid |
| 446C | 547 | 9-oxo-7a,7b-bishomo-15-hydroxy-15-methyl-cis-17,18-methano-13-trans-prostenoic acid and 9α,15-dihydroxy-7a,7b-bishomo-15-methyl-cis,17,18-methano-13-trans-prostenoic acid |
| 446D | 548 | 9-oxo-2-ethyl-15-hydroxy-15-methyl-cis-17,18-methano-13-trans-prostenoic acid and 9α,15-dihydroxy-2-ethyl-15-methyl-cis-17,18-methano-13-trans-prostenoic acid |
| 446E | 549 | 9-oxo-10a-homo-15-hydroxy-15-methyl-cis-17,18-methano-13-trans-prostenoic acid and 9α,15-dihydroxy-10a-homo-15-methyl-cis-17,18-methano-13-trans-prostenoic acid |
| 446F | 550 | 9-oxo-2-methyl-15-hydroxy-15-methyl-cis-17,18-methano-13-trans-prostenoic acid and 9α,15-dihydroxy-2-methyl-15-methyl-cis-17,18-methano-13-trans-prostenoic acid |
| 446G | 551 | 9-oxo-3,3-dimethyl-15-hydroxy-15-methyl-cis-17,18-methano-13-trans-prostenoic acid and 9α,15-dihydroxy-3,3-dimethyl-15-methyl-cis-17,18-methano-13-trans-prostenoic acid |
| 446H | 552 | 9-oxo-3-oxa-15-hydroxy-15-methyl-cis-17,18-methano-13-trans-prostenoic acid and 9α,15-dihydroxy-3-oxa-15-methyl-cis-17,18-methano-13-trans-prostenoic acid |
| 446I | 553 | 9-oxo-3-thia-15-hydroxy-15-methyl-cis-17,18-methano-13-trans-prostenoic acid and 9α,15-dihydroxy-3-thia-15-methyl-cis-17,18-methano-13-trans-prostenoic acid |
| 446J | 554 | 9-oxo-2-fluoro-15-hydroxy-15-methyl-cis,17,18-methano-13-trans-prostenoic acid and 9α,15-dihydroxy-2-fluoro-15-methyl-cis-17,18-methano-13-trans-prostenoic acid |
| 446K | 555 | 9-oxo-2-phenyl-15-hydroxy-15-methyl-cis-17,18-methano-13-trans-prostenoic acid and 9α,15-dihydroxy-2-phenyl-15-methyl-cis-17,18-methano-13-trans-prostenoic acid |
| 446L | 558 | 9-oxo-4-nor-15-hydroxy-15-methyl-cis-17,18-methano-5-cis,13-trans-prostadienoic acid and 9α,15-dihydroxy-4-nor-15-methyl-cis-17,18-methano-5-cis,13-trans-prostadienoic acid |
| 446M | 559 | 9-oxo-4a-homo-15-hydroxy-15-methyl-cis-17,18-methano-5-cis,13-trans-prostadienoic acid and 9α,15-dihydroxy-4a-homo-15-methyl-cis-17,18-methano-5-cis,13-trans-prostadienoic acid |
| 446N | 560 | 9-oxo-15-hydroxy-15-methyl-cis-17,18-methano-5-cis,13-trans-prostadienoic acid and 9α,15-dihydroxy-15-methyl-cis-17,18-methano-5-cis,13-trans-prostadienoic acid |
| 446P | 561 | 9-oxo-4a,4b-bishomo-15-hydroxy-15-methyl-cis-17,18-methano-5-cis,13-trans-prostadienoic acid and 9α,15-dihydroxy-4a,4b-bishomo-15-methyl-cis-17,18-methano-5-cis,13-trans-prostadienoic acid |

EXAMPLE 447

Preparation of
9-oxo-15-hydroxy-17,21-methanoprostanoic acid

A 2 g. sample of 9-oxo-15-hydroxy-17,20-methano-13-trans-prostenoic acid (Example 102) is hydrogenated using 700 mg. of 10% palladium on carbon in 50 ml. of absolute alcohol. The catalyst is removed by filtration and the mother liquor is taken to dryness to give 2 g. of subject compound as an oil.

EXAMPLES 448-512

Catalytic hydrogenation with 10% palladium-on-carbon catalyst by the procedure described in Example 447 of the various prostenoic acids or esters listed below in Table 12 provides the corresponding product prostenoic acids or esters of the table.

TABLE 12

| Example | Starting prostenoic acid or ester of example | Product 15-hydroxy-prostanoic acid or ester |
|---|---|---|
| 448 | 247 | 9-oxo-15-hydroxy-16,19-methano-20-nor-prostanoic acid |
| 449 | 248 | 9-oxo-15-hydroxy-18,20-ethano-prostanoic acid |
| 450 | 249 | 9-oxo-15-hydroxy-19,20-(1,3-propano)-prostanoic acid |
| 451 | 250 | 9-oxo-15-hydroxy-16-methyl-18,20-ethano-prostanoic acid |
| 452 | 251 | 9-oxo-15-hydroxy-17,20-ethano-prostanoic acid |
| 453 | 252 | 9-oxo-15-hydroxy-17,20-(1,3-propano)-prostanoic acid |
| 454 | 253 | 9-oxo-15-hydroxy-17,20-ethano-20-methyl-prostanoic acid |
| 455 | 254 | 9-oxo-15-hydroxy-17,18,19,20-tetranor-16-(1-adamantyl)-prostanoic acid |
| 456 | 255 | 9-oxo-15-hydroxy-16,20-methano-prostanoic acid |
| 457 | 256 | 9-oxo-15-hydroxy-16,19-ethano-prostanoic acid |
| 458 | 257 | 9-oxo-15-hydroxy-16,20-(1,3-propano)-prostanoic acid |
| 459 | 263 | 9-oxo-15-hydroxy-16,17,18,19,20-pentanor-15-(1-adamantyl)-prostanoic acid |
| 460 | 264 | 9-oxo-5,6,7-trinor-15-hydroxy-20,20-(1,4-butano)-prostanoic acid |
| 461 | 265 | 9-oxo-6,7-dinor-15-hydroxy-20-cyclopentyl-prostanoic acid |
| 462 | 266 | 9-oxo-7a,7b-bishomo-15-hydroxy-18-methyl-17,20-methano-prostanoic acid |
| 463 | 267 | 9-oxo-7a,7b-bishomo-15-hydroxy-16,19-ethano-prostanoic acid |
| 464 | 268 | 9-oxo-10a-homo-15-hydroxy-17,19-(1,3-propano)-prostanoic acid |
| 465 | 269 | 9-oxo-10a-homo-15-hydroxy-17,18,19,20-tetranor-16-(1-adamantyl)-prostanoic acid |
| 466 | 270 | 9-oxo-2-ethyl-15-hydroxy-17,20-ethano-prostanoic acid |
| 467 | 273 | 9-oxo-2-methyl-15-hydroxy-16-ethyl-19,20-(1,3-propano)-prostanoic acid |
| 468 | 274 | 9-oxo-2-methyl-15-hydroxy-17,19-methano-20-nor-prostanoic acid |
| 469 | 275 | 9-oxo-2-methyl-15-hydroxy-16,20-(1,3-propano)-prostanoic acid |
| 470 | 276 | 9-oxo-3,3-dimethyl-15-hydroxy-16,20-methano-prostanoic acid |
| 471 | 277 | 9-oxo-3,3-dimethyl-15-hydroxy-17,20-(1,4-butano)-prostanoic acid |
| 472 | 279 | 9-oxo-3-oxa-15-hydroxy-16,19-ethano-prostanoic acid |
| 473 | 280 | 9-oxo-3-oxa-15-hydroxy-17,18,19,20-tetranor-16-(1-adamantyl)-prostanoic acid |
| 474 | 281 | 9-oxo-3-oxa-15-hydroxy-20-methyl-19,20-(1,3-propano)-prostanoic acid |
| 475 | 282 | 9-oxo-3-oxa-15-hydroxy-16-ethyl-19,20-(1,3-propano)-prostanoic acid |
| 476 | 288 | 9-oxo-2-fluoro-15-hydroxy-20-methyl-17,20-(1,3-propano)-prostanoic acid |
| 477 | 289 | 9-oxo-2-fluoro-15-hydroxy-16,17,18,19,20-pentanor-15-(2-adamantyl)-prostanoic acid |
| 478 | 290 | 9-oxo-2-phenyl-15-hydroxy-16,20-methano-prostanoic acid |
| 479 | 174 | decyl 9-oxo-15-hydroxy-20-nor-16,19-methano-prostanoate |
| 480 | 211 | butyl 9-oxo-15-hydroxy-16,20-ethanoprostanoate |
| 481 | 199 | ethyl 9-oxo-3-oxa-15-hydroxy-16,19-ethano-prostanoate |
| 481a | 103 | 9-oxo-15-epi-hydroxy-17,20-methano-prostanoate |
| 482 | 326 | 9α,15-dihydroxy-16,19-methano-20-nor-prostanoic acid |
| 483 | 327 | 9α,15-dihydroxy-18,20-ethano-prostanoic acid |
| 497 | 347 | 10a-homo-9α,15-dihydroxy-17,19-(1,3-propano)-prostanoic acid |
| 498 | 348 | 10a-homo-9α,15-dihydroxy-17,18,19,20-tetranor-16-(1-adamantyl)-prostanoic acid |
| 499 | 349 | 2-ethyl-9α,15-dihydroxy-17,20-ethano-prostanoic acid |
| 500 | 352 | 2-methyl-9α,15-dihydroxy-16-ethyl-19,20-(1,3-propano)-prostanoic acid |
| 501 | 353 | 2-methyl-9α,15-dihydroxy-17,19-methano-20-nor-prostanoic acid |
| 502 | 354 | 2-methyl-9α,15-dihydroxy-16,20-(1,3-propano)-prostanoic acid |
| 503 | 355 | 3,3-dimethyl-9α,15-dihydroxy-16,20-methano-prostanoic acid |
| 504 | 356 | 3,3-dimethyl-9α,15-dihydroxy-17,20-(1,4-butano)-prostanoic acid |
| 505 | 358 | 3-oxa-9α,15-dihydroxy-16,19-ethano-prostanoic acid |
| 506 | 359 | 3-oxa-9α,15-dihydroxy-17,18,19,20-tetranor-16-(1-adamantyl)-prostanoic acid |
| 507 | 360 | 3-oxa-9α,15-dihydroxy-20-methyl-19,20-(1,3-propano)-prostanoic acid |
| 508 | 361 | 3-oxa-9α,15-dihydroxy-16-ethyl-19,20-(1,3-propano)-prostanoic acid |

TABLE 12-continued

| Example | Starting prostenoic acid or ester of example | Product 15-hydroxy-prostanoic acid or ester |
|---|---|---|
| 509 | 325 | 9α,15-dihydroxy-17,20-methano-prostanoic acid |
| 510 | 413* | 9-oxo-15-hydroxy-15-methyl-18,20-ethano-prostanoic acid |
| 511 | 414* | 9-oxo-15-hydroxy-15-methyl-19,20-(1,3-propano)-prostanoic acid |
| 512 | 430* | 9-oxo-3-oxa-15-hydroxy-15-methyl-19,20-(1,3-propano)-prostanoic acid |
| 512a | 375a | 9α,15-epi-dihydroxy-17,20-methano-prostanoic acid |

*9-oxo product of this example.

EXAMPLES 513–542

Treatment of the prostenoic or prostanoic acids listed in Table 13 below with the indicated diazoalkane in the following manner provides the product esters of the table.

An ethereal solution containing a molar excess of diazoalkane is added to a solution of prostenoic acid in ether (or acetone). After two to four hours the solution is carefully evaporated under reduced pressure and the residual ester is purified in the usual way by chromatography on silica gel.

TABLE 13

| Example | Starting acid of Example | Diazoalkane | Product Ester |
|---|---|---|---|
| 513 | 250 | diazodecane | decyl 9-oxo-15-hydroxy-16-methyl-18,20-ethano-13-trans-prostenoate |
| 514 | 256 | diazoheptane | heptyl 9-oxo-15-hydroxy-16,19-ethano-13-trans-prostenoate |
| 515 | 262 | diazoheptane | heptyl 9-oxo-15-hydroxy-16,20-methano-13-trans,18-prostadienate |
| 516 | 267 | diazodecane | decyl 9-oxo-7α,7β-bishomo-16,19-ethano-13-trans-prostenoate |
| 517 | 282 | diazopentane | pentyl 9-oxo-3-oxa-15-hydroxy-16-ethyl-19,20-(1,3-propano)-prostenoate |
| 518 | 285 | diazodecane | decyl 9-oxo-3-thia-15-hydroxy-16-methyl-18,20-ethano-prostenoate |
| 519 | 296 | diazodecane | decyl 9-oxo-4a-homo-15-hydroxy-16,20-methano-5-cis,13-trans-prostadienoate |
| 520 | 300 | diazodecane | decyl 9-oxo-15-hydroxy-16-ethyl-19,20-(1,3-propanO)-5-cis,13-trans-prostadienoate |
| 521 | 309 | diazoheptane | heptyl 9-oxo-15-hydroxy-16,19-ethano-5-cis,13-trans-prostadienoate |
| 522 | 309 | diazopentane | pentyl 9-oxo-15-hydroxy-16,19-ethano-5-cis,13-trans-prostadienoate |
| 523 | 309 | diazodecane | decyl 9-oxo-15-hydroxy-16,19-ethano-5-cis,13-trans-prostadienoate |
| 524 | 314 | diazodecane | decyl 9-oxo-15-hydroxy-16-methyl-16,20-methano-5-cis,13-trans-prostadienoate |
| 525 | 335 | diazodecane | decyl 9α,15-dihydroxy-16,19-ethano-13-trans-prostenoate |
| 526 | 335 | diazopentane | pentyl 9α,15-dihydroxy-16,19-ethano-13-trans-prostenoate |
| 527 | 335 | diazopentane | heptyl 9α,15-dihydroxy-16,19-ethano-13-trans-prostenoate |
| 528 | 379 | diazoheptane | heptyl 9α,15-dihydroxy-16-ethyl-19,20-(1,3-propano)-5-cis,13-trans-prostadienoate |
| 529 | 386 | diazoheptane | heptyl 9α,15-dihydroxy-16,20-methano-5-cis,13-trans-prostadienoate |
| 530 | 413 | diazodecane | decyl 9-oxo-15-hydroxy-15-methyl-18,20-ethano-13-trans-prostenoate |
| 531 | 414 | diazodecane | decyl 9-oxo-15-hydroxy-15-methyl-19,20-(1,3-propano-13-trans-prostenoate |
| 532 | 437 | diazodecane | decyl 9-oxo-15-hydroxy-15-methyl-18,20-ethano-5-cis,13-trans-prostadienoate |
| 533 | 437 | diazopentane | pentyl 9-oxo-15-hydroxy-15-methyl-18,20-ethano-5-cis,13-trans-prostadienoate |
| 534 | 437 | diazoheptane | heptyl 9-oxo-15-hydroxy-15-methyl-18,20-ethano-5-cis,13-trans-prostadienoate |
| 535 | 439 | diazoheptane | heptyl 9-oxo-15-hydroxy-15-methyl-19,20-(1,4-butano)-5-cis,13-trans-prostadienoate |
| 535A | 441 | diazoheptane | heptyl 9-oxo-15-hydroxy-15-methyl-17,20-methano-5-cis,13-trans-prostadienoate |
| 536 | 457 | diazodecane | decyl 9-oxo-15-hydroxy-16,19-ethano-prostanoate |
| 537 | 448 | diazoheptane | heptyl 9-oxo-15-hydroxy-16,19-methano-20-nor-prostanoate |
| 538 | 464 | diazoheptane | heptyl 9-oxo-10a-homo-15-hydroxy-17,19-(1,3-propano)-prostanoate |
| 539 | 102 | diazodecane | decyl 9-oxo-15-hydroxy-17,20-methano-13-trans-prostenoate |

TABLE 13-continued

| Example | Starting acid of Example | Diazoalkane | Product Ester |
|---|---|---|---|
| 540 | 102 | diazoheptane | heptyl 9-oxo-15-hydroxy-17,20-methano-13-trans-prostenoate |
| 541 | 103 | diazodecane | decyl 9-oxo-15-epi-hydroxy-17,20-methano-13-trans-prostenoate |
| 542 | 103 | diazoheptane | heptyl 9-oxo-15-epi-hydroxy-17,20-methano-13-trans-prostenoate |

EXAMPLE 543

Treatment of 1-iodo-3-triphenylmethoxy-cis-5,6-methylene-trans-1-octene (Example 86) with butyl lithium by the procedure described in Example 101 is productive of 3-triphenylmethoxy-cis-5,6-methylene-trans-1-octenyl lithium, which on treatment with trimethyl aluminum by the procedure described in Example 101 furnishes lithio(3-triphenylmethoxy-cis-5,6-methylene-trans-1-octenyl)trimethyl alanate.

EXAMPLES 544–561

Treatment of the cycloalkenone listed in Table 14 below with lithio(3-triphenylmethoxy-cis-5,6-methylene-trans-1-octenyl)trimethyl alanate (Example 543) followed by acid-catalyzed de-O-tritylation of the intermediate alkyl 9-oxo-15-triphenylmethoxy-13-trans-prostenoate is productive of the alkyl 9-oxo-15-hydroxy-cis-17,18-methano-13-trans-prostenoates of the table. The entire sequence is carried out by the procedures described in Example 101.

TABLE 14

| Example | Starting cycloalkenone | Product alkyl 9-oxo-15-hydroxy-cis-17,18-methano-13-trans-prostenoate |
|---|---|---|
| 544 | 2-(6-carbethoxyhexyl)cyclopent-2-en-1-one* | ethyl 9-oxo-15-hydroxy-cis-17,18-methano-13-trans-prostenoate |
| 545 | 2-(6-carbo-n-decyloxyhexyl)cyclopent-2-en-1-one (Example 7) | decyl 9-oxo-15-hydroxy-cis-17,18-methano-13-trans-prostenoate |
| 546 | 2-(4-carbethoxybutyl)cyclopent-2-en-1-one* | ethyl 9-oxo-6,7-dinor-15-hydroxy-cis-17,18-methano-13-trans-prostenoate |
| 547 | 2-(8-carbethoxyocytl)cyclopent-2-en-1-one* | ethyl 9-oxo-7a,7b-bishomo-15-hydroxy-cis-17,18-methano-13-trans-prostenoate |
| 548 | 2-(6-carbethoxyoctyl)cyclopent-2-en-1-one* | ethyl 9-oxo-2-ethyl-15-hydroxy-cis-17,18-methano-13-trans-prostenoate |
| 549 | 2-(6-carbethoxyhexyl)cyclohex-2-en-1-one* | ethyl 9-oxo-10a-homo-15-hydroxy-cis-17,18-methano-13-trans-prostenoate |
| 550 | 2-(6-carbethoxyheptyl)cyclopent-2-en-1-one (Example 3) | ethyl 9-oxo-2-methyl-15-hydroxy-cis-17,18-methano-13-trans-prostenoate |
| 551 | 2-(6-carbethoxy-5,5-dimethylhexyl)cyclopent-2-en-1-one* | ethyl 9-oxo-3,3-dimethyl-15-hydroxy-cis-17,18-methano-13-trans-prostenoate |
| 552 | 2-(6-carbethoxy-5-oxahexyl)cyclopent-2-en-1-one* | ethyl 9-oxo-3-oxa-15-hydroxy-cis-17,18-methano-13-trans-prostenoate |
| 553 | 2-(6-carbethoxy-5-thiahexyl)cyclopent-2-en-1-one* | ethyl 9-oxo-3-thia-15-hydroxy-cis-17,18-methano-13-trans-prostenoate |
| 554 | 2-(6-carbethoxy-6-fluorohexyl)cyclopent-2-en-1-one (Example 1) | ethyl 9-oxo-2-fluoro-15-hydroxy-cis-17,18-methano-13-trans-prostenoate |
| 555 | 2-(6-carbethoxy-6-phenylhexyl)cyclopent-2-en-1-one (Example 2) | ethyl 9-oxo-2-phenyl-15-hydroxy-cis-17,18-methano-13-trans-prostenoate |
| 556 | 2-(6-carbo-n-butoxyhexyl)cyclopent-2-en-1-one (Example 4) | butyl 9-oxo-15-hydroxy-cis-17,18-methano-13-trans-prostenoate |
| 557 | 2-(6-carboisopropoxyhexyl)cyclopent-2-en-1-one (Example 5) | isopropyl 9-oxo-15-hydroxy-cis-17,18-methano-13-trans-prostenoate |
| 558 | 2-(5-carbomethoxy-2-cis-pentenyl)cyclopent-2-en-1-one (Example 28) | methyl 9-oxo-4-nor-15-hydroxy-cis-17,18-methano-5-cis,13-trans-prostadienoate |
| 559 | 2-(7-carbomethoxy-2-cis-heptenyl)cyclopent-2-en-1-one (Example 29) | methyl 9-oxo-4a-homo-15-hydroxy-cis-17,18-methano-5-cis,13-trans-prostadienoate |
| 560 | 2-(6-carbomethoxy-2-cis-hexenyl)cyclopent-2-en-1-one (Example 14) | methyl 9-oxo-15-hydroxy-cis-17,18-methano-5-cis,13-trans-prostadienoate |
| 561 | 2-(6-carbomethoxy-2-cis-octenyl)cyclopent-2-en-1-one (Example 30) | methyl 9-oxo-4a,4b-bishomo-15-hydroxy-cis-17,18-methano-5-cis,-13-trans-prostadienoate |

*Belgium Patent No. 786,215 (January 15, 1973).

EXAMPLES 562–576

Saponification by the procedure described in Example 102 of the alkyl esters listed in Table 15 below provides the product 9-oxo-15-hydroxy-cis-17,18-methano-13-trans-prostenoic acids of the table.

TABLE 15

| Ex. | Starting Alkyl Ester of Example | Product 9-oxo-15-hydroxy-cis-17,18-methano-13-trans-prostenoic acid |
|---|---|---|
| 562 | 544 | 9-oxo-15-hydroxy-cis-17,18-methano-13-trans-prostenoic acid |
| 563 | 546 | 9-oxo-6,7-dinor-15-hydroxy-cis-17,18-methano-13-trans-prostenoic acid |
| 564 | 547 | 9-oxo-7a,7b-bishomo-15-hydroxy-cis-17,18-methano-13-trans- |

TABLE 15-continued

| Ex. | Starting Alkyl Ester of Example | Product 9-oxo-15-hydroxy-cis-17,18-methano-13-trans-prostenoic acid |
|---|---|---|
| 565 | 548 | 9-oxo-2-ethyl-15-hydroxy-cis-17,18-methano-13-trans-prostenoic acid |
| 566 | 549 | 9-oxo-10a-homo-15-hydroxy-cis-17,18-methano-13-trans-prostenoic acid |
| 567 | 550 | 9-oxo-2-methyl-15-hydroxy-cis-17,18-methano-13-trans-prostenoic acid |
| 568 | 551 | 9-oxo-3,3-dimethyl-15-hydroxy-cis-17,18-methano-13-trans-prostenoic acid |
| 569 | 552 | 9-oxo-3-oxa-15-hydroxy-cis-17,18-methano-13-trans-prostenoic acid |
| 570 | 553 | 9-oxo-3-thia-15-hydroxy-cis-17,18-methano-13-trans-prostenoic acid |
| 571 | 554 | 9-oxo-2-fluoro-15-hydroxy-cis-17,18-methano-13-trans-prostenoic acid |
| 572 | 555 | 9-oxo-2-phenyl-15-hydroxy-cis-17,18-methano-13-trans-prostenoic acid |
| 573 | 558 | 9-oxo-4-nor-15-hydroxy-cis-17,18-methano-5-cis,13-trans-prostadienoic acid |
| 574 | 559 | 9-oxo-4a-homo-15-hydroxy-cis-17,18-methano-5-cis,13-trans-prostadienoic acid |
| 575 | 560 | 9-oxo-15-hydroxy-cis-17,18-methano-5-cis,13-trans-prostadienoic acid |
| 576 | 561 | 9-oxo-4a,4b-bishomo-15-hydroxy-cis-17,18-methano-5-cis,13-trans-prostadienoic acid |

EXAMPLES 577–591

Treatment of the 9-oxo derivatives listed below in Table 16 with lithium perhydro-9b-boraphenalyl hydride by the procedure described in Example 325 provides the product 9α,15-dihydroxy-cis-17,18-methano-prostenoic acids of the table.

TABLE 10

| Example | Starting 9-oxo derivative of Example | Product 9α,15-dihydroxy-cis-17,18-methano-13-trans-prostenoic acid |
|---|---|---|
| 577 | 562 | 9α,15-dihydroxy-cis-17,18-methano-13-trans-prostenoic acid |
| 578 | 563 | 9α,15-dihydroxy-6,7-dinor-cis-17,18-methano-13-trans-prostenoic acid |
| 579 | 564 | 9α,15-dihydroxy-7a,7b-bishomo-cis-17,18-methano-13-trans-prostenoic acid |
| 580 | 565 | 9α,15-dihydroxy-2-ethyl-cis-17,18-methano-13-trans-prostenoic acid |
| 581 | 566 | 9α,15-dihydroxy-10a-homo-cis-17,18-methano-13-trans-prostenoic acid |
| 582 | 567 | 9α,15-dihydroxy-2-methyl-cis-17,18-methano-13-trans-prostenoic acid |
| 583 | 568 | 9α,15-dihydroxy-3,3-dimethyl-cis-17,18-methano-13-trans-prostenoic acid |
| 584 | 569 | 9α,15-dihydroxy-3-oxa-cis-17,18-methano-13-trans-prostenoic acid |
| 585 | 570 | 9α,15-dihydroxy-3-thia-cis-17,18-methano-13-trans-prostenoic acid |
| 586 | 571 | 9α,15-dihydroxy-2-fluoro-cis-17,18-methano-13-trans-prostenic acid |
| 587 | 572 | 9α,15-dihydroxy-2-phenyl-cis-17,18-methano-13-trans-prostenoic acid |
| 588 | 573 | 9α,15-dihydroxy-4-nor-cis-17,18-methano-5-cis,13-trans-prostadienoic acid |
| 589 | 574 | 9α,15-dihydroxy-4a-homo-cis-17,18-methano-5-cis,13-trans-prostadienoic acid |
| 590 | 575 | 9α,15-dihydroxy-cis-17,18-methano-5-cis,13-trans-prostadienoic acid |
| 591 | 576 | 9α,15-dihydroxy-4a,4b-bishomo-cis-17,18-methano-5-cis,13-trans-prostadienoic acid |

EXAMPLES 592–628

Hydrogenation of the 13-trans-prostenoic acids or esters listed in Table 17 below in the presence of 10% palladium-on-carbon catalyst by the procedure described in Example 447 furnishes the product prostanoic acid and ester of the table.

TABLE 17

| Example | Starting 13-trans-prostenoic acid or ester of Example | Product prostanoic acid or ester |
|---|---|---|
| 592 | 544 | ethyl 9-oxo-15-hydroxy-cis-17,18-methano-prostanoate |
| 593 | 545 | decyl 9-oxo-15-hydroxy-cis-17,18-methano-prostanoate |
| 594 | 563 | 9-oxo-6,7-dinor-15-hydroxy-cis-17,18-methano-prostanoic acid |
| 595 | 564 | 9-oxo-7a,7b-bishomo-15-hydroxy-cis-17,18-methano-prostanoic acid |
| 596 | 565 | 9-oxo-2-ethyl-15-hydroxy-cis-17,18-methano-prostanoic acid |
| 597 | 566 | 9-oxo-10a-homo-15-hydroxy-cis-17,18-methano-prostanoic acid |
| 598 | 567 | 9-oxo-2-methyl-15-hydroxy-cis-17,18-methano-prostanoic acid |
| 599 | 568 | 9-oxo-3,3-dimethyl-15-hydroxy-cis-17,18-methano-prostanoic |

TABLE 17-continued

| Example | Starting 13-trans-prostenoic acid or ester of Example | Product prostanoic acid or ester |
|---|---|---|
| 600 | 569 | 9-oxo-3-oxa-15-hydroxy-cis-17,18-methano-prostanoic acid |
| 601 | 570 | 9-oxo-3-thia-15-hydroxy-cis-17,18-methano-prostanoic acid |
| 602 | 571 | 9-oxo-2-fluoro-15-hydroxy-cis-17,18-methano-prostanoic acid |
| 603 | 572 | 9-oxo-2-phenyl-15-hydroxy-cis-17,18-methano-prostanoic acid |
| 604 | 556 | butyl 9-oxo-15-hydroxy-cis-17,18-methano-prostanoic acid |
| 605 | 557 | isopropyl 9-oxo-15-hydroxy-cis-17,18-methano-prostanoic acid |
| 606 | 562 | 9-oxo-15-hydroxy-cis-17,18-methano-prostanoic acid |
| 607 | 577 | 9α,15-dihydroxy-cis-17,18-methano-prostanoic acid |
| 608 | 578 | 9α,15-dihydroxy-6,7-dinor-cis-17,18-methano-prostanoic acid |
| 609 | 579 | 9α,15-dihydroxy-7a,7b-bishomo-cis-17,18-methano-prostanoic acid |
| 610 | 580 | 9α,15-dihydroxy-2-ethyl-cis-17,18-methano-prostanoic acid |
| 611 | 581 | 9α,15-dihydroxy-10a-homo-cis-17,18-methano-prostanoic acid |
| 612 | 582 | 9α,15-dihydroxy-2-methyl-cis-17,18-methano-prostanoic acid |
| 613 | 583 | 9α,15-dihydroxy-3,3-dimethyl-cis-17,18-methano-prostanoic acid |
| 614 | 584 | 9α,15-dihydroxy-3-oxa-cis-17,18-methano-prostanoic acid |
| 615 | 585 | 9α,15-dihydroxy-3-thia-cis-17,18-methano-Prostanoic acid |
| 616 | 586 | 9α,15-dihydroxy-2-fluoro-cis-17,18-methano-prostanoic acid |
| 617 | 587 | 9α,15-dihydroxy-2-phenyl-cis-17,18-methano-prostanoic acid |
| 618 | 446A* | 9α,15-dihydroxy-15-methyl-cis-17,18-methano-prostanoic acid |
| 619 | 446H* | 9α,15-dihydroxy-15-methyl-3-oxa-cis-17,18-methano-prostanoic acid |
| 620 | 446I* | 9α,15-dihydroxy-15-methyl-3-thia-cis-17,18-methano-prostanoic acid |
| 621 | 446G* | 9α,15-dihydroxy-15-methyl-3,3-dimethyl-cis-17,18-methano-prostanoic acid |
| 622 | 446F* | 9α,15-dihydroxy-15-methyl-2-methyl-cis-17,18-methano-prostanoic acid |
| 623 | 446A** | 9-oxo-15-hydroxy-15-methyl-cis-17,18-methano-prostanoic acid |
| 624 | 446C** | 9-oxo-15-hydroxy-15-methyl-7a,7b-bishomo-cis-17,18-methano-prostanoic acid |
| 625 | 446D** | 9-oxo-15-hydroxy-15-methyl-2-ethyl-cis-17,18-methano-prostanoic acid |
| 626 | 446G** | 9-oxo-15-hydroxy-15-methyl-3,3-dimethyl-cis-17,18-methano-prostanoic acid |
| 627 | 446H** | 9-oxo-15-hydroxy-15-methyl-3-oxa-cis-17,18-methano-prostanoic acid |
| 628 | 446I** | 9-oxo-15-hydroxy-15-methyl-3-thia-cis-17,18-methano-prostanoic acid |

*9α,15-dihydroxy product of this example only.
**9-oxo product of this example only.

We claim:
1. An optically active compound of the formula:

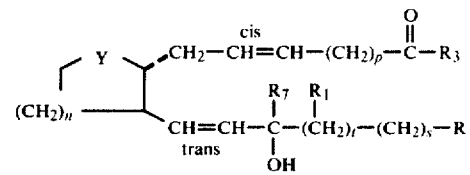

or a racemic compound of that formula and the mirror image thereof wherein n is the integer 1 or 2; Y is a divalent radical selected from the group consisting of those of the formulae:

$$\underset{/\ \backslash}{\overset{HO\ \ \ \ H}{\underset{C}{\diagup\!\diagdown}}} \quad \text{and} \quad \underset{/\ \backslash}{\overset{H\ \ \ \ OH}{\underset{C}{\diagup\!\diagdown}}} \ ;$$

p is an integer from 2 to 6, inclusive; $R_1$ is an alkyl group having up to 3 carbon atoms; $R_3$ is selected from the group consisting of hydroxy and alkoxy having from one to twelve carbon atoms; $R_7$ is selected from the group consisting of hydrogen and a lower alkyl group having up to 3 carbon atoms; s is zero or an integer from one to five inclusive; t is zero or one; and R is selected from the group consisting of cycloalkyl having from three to nine carbon atoms, cycloalkenyl having from five to nine carbon atoms, mono- or di-lower alkyl substituted cycloalkyl having from three to eight carbon atoms in the ring, and mono- or di-lower alkyl substituted cycloalkenyl having from five to eight carbon atoms in the ring; with the proviso that only one double bond or cyclopropyl group can be immediately adjacent to $C_{15}$; and the pharmaceutically acceptable cationic salts thereof when $R_3$ is hydroxy.

2. An optically active compound according to claim 1, wherein Z, m, $R_1$, $R_3$, $R_7$, s and t are as previously defined; n is the integer1; Y is the divalent radical

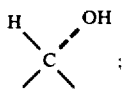

p is the integer 3; and R is selected from the group consisting of cycloalkyl having from three to nine carbon atoms and cycloalkenyl having from five to nine carbon atoms.

3. An optically active compound according to claim 2, wherein $R_1$, $R_3$, s, t, n, Y, p, $C_{13}$–$C_{14}$ and R are as previously defined; and $R_7$ is selected from the group consisting of hydrogen and methyl.

4. The racemic compound according to claim 1, dl-9α,15-dihydroxy-20,20-(1,4-butano)-5-cis,13-trans-prostadienoic acid.

5. The optically active compound according to claim 1, l-9α, 15-dihydroxy-20,20-(1,4-butano)-5-cis,13-trans-prostadienoic acid.

6. The racemic compound according to claim 1, dl-9α,15-dihydroxy-20-cyclopentyl-5-cis,13-trans-prostadienoic acid.

7. The optically active compound according to claim 1, l-9α,15-dihydroxy-20-cyclopentyl-5-cis,13-trans-prostadienoic acid.

8. The racemic compound according to claim 1, dl-9α,15-dihydroxy-17,20-ethano-5-cis,13-trans-prostadienoic acid.

9. The optically active compound according to claim 1, l-9α,15-dihydroxy-17,20-ethano-5-cis,13-trans-prostadienoic acid.

10. The racemic compound according to claim 1, dl-9α,15-dihydroxy-19,20-(1,4-butano)-5-cis,13-trans-prostadienoic acid.

11. The optically active compound according to claim 1, l-9α,15-dihydroxy-19,20-(1,4-butano)-5-cis,13-trans-prostadienoic acid.

12. The racemic compound according to claim 1, dl-9α,15-dihydroxy-17,20-(1,3-propano)-5-cis,13-trans-prostadienoic acid.

13. The optically active compound according to claim 1, l-9α,15-dihydroxy-17,20-(1,3-propano)-5-cis,13-trans-prostadienoic acid.

14. The racemic compound according to claim 1, dl-9α,15-dihydroxy-20-methyl-17,20-ethano-5-cis,13-trans-prostadienoic acid.

15. The optically active compound according to claim 1, l-9α,15-dihydroxy-20-methyl-17,20-ethano-5-cis,13-trans-prostadienoic acid.

16. The racemic compound according to claim 1, dl-9α,15-dihydroxy-17-methyl-20-nor-16,18-ethano-5-cis,13-trans-prostadienoic acid.

17. The optically active compound according to claim 1, l-9α,15-dihydroxy-17-methyl-20-nor-16,18-ethano-5-cis,13-trans-prostadienoic acid.

18. The racemic compound according to claim 1, dl-9α,15-dihydroxy-16,20-methano-5-cis,13-trans-prostadienoic acid.

19. The optically active compound according to claim 1, l-9α,15-dihydroxy-16,20-methano-5-cis,13-trans-prostadienoic acid.

20. The racemic compound according to claim 1, dl-9α,15-dihydroxy-17,20-methano-5-cis,13-trans-prostadienoic acid.

21. The optically active compound according to claim 1, l-9α,15-dihydroxy-17,20-methano-5-cis,13-trans-prostadienoic acid.

22. The racemic compound according to claim 1, dl-9α,15-dihydroxy-16,19-ethano-5-cis,13-trans-prostadienoic acid.

23. The racemic compound according to claim 1, dl-9α,15-dihydroxy-16,20-ethano-5-cis,13-trans-prostadienoic acid.

24. The optically active compound according to claim 1, l-9α,15-dihydroxy-16,20-ethano-5-cis,13-trans-prostadienoic acid.

25. The racemic compound according to claim 1, dl-9α,15-dihydroxy-16-methyl-16,20-methano-5-cis,13-trans-prostadienoic acid.

26. The racemic compound according to claim 1, dl-9α,15-dihydroxy-15-methyl-20-cyclopentyl-5-cis,13-trans-prostadienoic acid.

27. The optically active compound according to claim 1, l-9α,15-dihydroxy-15-methyl-20-cyclopentyl-5-cis,13-trans-prostadienoic acid.

28. The racemic compound according to claim 1, dl-9α,15-dihydroxy-15-methyl-19,20-(1,4-butano)-5-cis,13-trans-prostadienoic acid.

29. The optically active compound according to claim 1, l-9α,15-dihydroxy-15-methyl-19,20-(1,4-butano)-5-cis,13-trans-prostadienoic acid.

30. The racemic compound according to claim 1, dl-9α,15-dihydroxy-15-methyl-20-methyl-17,20-ethano-5-cis,13-trans-prostadienoic acid.

31. The optically active compound according to claim 1, l-9α,15-dihydroxy-15-methyl-20-methyl-17,20-ethano-5-cis,13-trans-prostadienoic acid.

32. The racemic compound according to claim 1, dl-9α,15-dihydroxy-15-methyl-17,20-methano-5-cis,13-trans-prostadienoic acid.

33. The optically active compound according to claim 1, l-9α,15-dihydroxy-15-methyl-17,20-methano-5-cis,13-trans-prostadienoic acid.

34. The racemic compound according to claim 1, dl-9α,15-dihydroxy-16-ethyl-19,20-(1,3-propano)-5-cis,13-trans-prostadienoic acid.

35. The optically active compound according to claim 1, l-9α,15-dihydroxy-16,19-ethano-5-cis,13-trans-prostadienoic acid.

36. The racemic compound according to claim 1, dl-9α,15-dihydroxy-16,20-(1,3-propano)-5-cis,13-trans-prostadienoic acid.

37. The optically active compound according to claim 1, l-9α,15-dihydroxy-16-methyl-16,20-methano-5-cis,13-trans-prostadienoic acid.

38. An optically active compound of the formula:

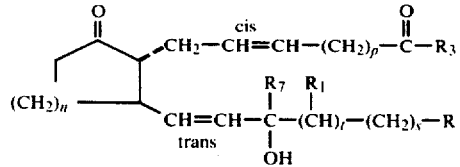

or a racemic compound of that formula and the mirror image thereof wherein n is the integer 1 or 2; p is an integer from 2 to 6 inclusive, $R_1$ is an alkyl group having up to 3 carbon atoms; $R_3$ is selected from the group consisting of hydroxy and alkoxy having from one to twelve carbon atoms; $R_7$ is selected from the group consisting of hydrogen and a lower alkyl group having up to 3 carbon atoms; s is zero or an integer from one to five inclusive; t is zero or one; and R is selected from the group consisting of cycloalkyl having from three to nine carbon atoms, cycloalkenyl having from five to nine carbon atoms, mono- or di-lower alkyl substituted cycloalkyl having from three to eight carbon atoms in the ring, and mono- or di-lower alkyl substituted cycloalkenyl having from five to eight carbon atoms in the ring; with the proviso that only one double bond or cyclopropyl group can be immediately adjacent to $C_{15}$; and the pharmaceutically acceptable cationic salts thereof when $R_3$ is hydroxy.

39. An optically active compound according to claim 38 wherein Z, m, $R_1$, $R_3$, $R_7$, s and t are as previously defined; n is the integer 1; p is the integer 3; and R is selected from the group consisting of cycloalkyl having from three to nine carbon atoms and cycloalkenyl having from five to nine carbon atoms.

40. An optically active compound according to claim 39, wherein m, $R_1$, $R_3$, s, t, n, $C_{13}$-$C_{14}$ and R are as previously defined; Z is the divalent radical—$(CH_2)_m$—; and $R_7$ is selected from the group consisting of hydrogen and methyl.

41. An optically active compound according to claim 39, wherein $R_1$, $R_3$, s, t, n, p, $C_{13}$-$C_{14}$ and R are as previously defined; and $R_7$ is selected from the group consisting of hydrogen and methyl.

42. The optically active compound according to claim 38, 1-9-oxo-15-hydroxy-16-ethyl-19,20-(1,3-propano)-5-cis,13-trans-prostadienoic acid.

43. The racemic compound according to claim 38, dl-9-oxo-15-hydroxy-16,19-ethano-5-cis,13-trans-prostadienoic acid.

44. The optically active compound according to claim 38, 1-9-oxo-15-hydroxy-16,20-(1,3-propano)-5-cis,13-trans-prostadienoic acid.

45. The racemic compound according to claim 38, dl-9-oxo-15-hydroxy-16,20-methano-5-cis,13-trans-prostadienoic acid.

46. The optically active compound according to claim 38, 1-9-oxo-15-hydroxy-15-methyl-18,20-ethano-5-cis,13-trans-prostadienoic acid.

47. The compound according to claim 38, 9-oxo-15-hydroxy-17,18-cis-methano-5-cis,13-trans-prostadienoic acid.

* * * * *